(12) United States Patent
Zhang

(10) Patent No.: US 10,016,389 B2
(45) Date of Patent: Jul. 10, 2018

(54) METHOD OF MAKING LIPOSOMES, LIPOSOME COMPOSITIONS MADE BY THE METHODS, AND METHODS OF USING THE SAME

(75) Inventor: Yuanpeng Zhang, Cupertino, CA (US)

(73) Assignee: LivOn Laboratories, Henderson, NV (US)

( * ) Notice: Subject to any disclaimer, the term of this patent is extended or adjusted under 35 U.S.C. 154(b) by 0 days.

(21) Appl. No.: 13/020,730

(22) Filed: Feb. 3, 2011

(65) Prior Publication Data

US 2012/0171280 A1    Jul. 5, 2012

Related U.S. Application Data

(60) Provisional application No. 61/430,024, filed on Jan. 5, 2011.

(51) Int. Cl.
| | | |
|---|---|---|
| *A61K 9/127* | (2006.01) |
| *A61K 31/375* | (2006.01) |
| *A61K 31/198* | (2006.01) |
| *A61K 31/385* | (2006.01) |

(52) U.S. Cl.
CPC ............ *A61K 31/375* (2013.01); *A61K 9/127* (2013.01); *A61K 31/198* (2013.01); *A61K 31/385* (2013.01)

(58) Field of Classification Search
CPC .................................................... A61K 9/127
USPC .......................................................... 424/450
See application file for complete search history.

(56) References Cited

U.S. PATENT DOCUMENTS

| | | | |
|---|---|---|---|
| 3,932,657 A | 1/1976 | Rahman | |
| 4,235,871 A | 11/1980 | Howard et al. | |
| 4,311,712 A | 1/1982 | Evans et al. | |
| 5,013,556 A | 5/1991 | Woodle et al. | |
| 5,395,619 A | 3/1995 | Zalipsky et al. | |
| 5,711,965 A * | 1/1998 | Ghyczy et al. | 424/450 |
| 6,596,305 B1 * | 7/2003 | Edgerly-Plug | 424/450 |
| 6,713,533 B1 * | 3/2004 | Panzner | 523/202 |
| 6,726,924 B2 | 4/2004 | Keller | |
| 7,744,920 B2 | 6/2010 | Barenholz et al. | |
| 2002/0198258 A1 * | 12/2002 | Brown | A61K 31/24 514/535 |
| 2003/0099694 A1 | 5/2003 | Gregor et al. | |
| 2003/0157220 A1 * | 8/2003 | Morello et al. | 426/72 |
| 2007/0104774 A1 | 5/2007 | Kim et al. | |
| 2009/0324698 A1 * | 12/2009 | Wagner | A61K 9/0034 424/450 |
| 2009/0324699 A1 | 12/2009 | Preswetoff-Morath et al. | |

FOREIGN PATENT DOCUMENTS

| | | |
|---|---|---|
| CA | 2067807 C | 11/1998 |
| CA | 2628777 A1 | 6/2006 |
| CN | 101721369 A | 6/2010 |

(Continued)

OTHER PUBLICATIONS

Kirby, C.J., et al, International Journal of Food Science and Technology, vol. 26, pp. 437-449, 1991.*

(Continued)

*Primary Examiner* — Gollamudi Kishore
(74) *Attorney, Agent, or Firm* — McDermott Will & Emery LLP

(57) ABSTRACT

A method of preparing liposomes, liposome compositions formed by the process, and methods of using the liposome composition are provided herein.

8 Claims, 4 Drawing Sheets

(56) References Cited

FOREIGN PATENT DOCUMENTS

| JP | 2003-119120 A | 4/2003 |
| JP | 2009545587 A | 12/2009 |
| WO | WO 1991/006310 A1 | 5/1991 |
| WO | WO 1996/008234 A1 | 3/1996 |
| WO | WO 2008/016258 A1 | 2/2008 |
| WO | WO 2009/088959 A1 | 7/2009 |

OTHER PUBLICATIONS

Empirical Labs, promotional brochure, "Liposomes 101", 1 page, accessed online on Aug. 30, 2010 from http://www.empirical-labs.com/v/vspfiles/assets/images/lipo.pdf.

Gingi™ catalog, "Gingi Vitamin C & E Liposome", 1 page, accessed online on Aug. 6, 2010 from http://www.gingiskincare.com/product-details.php?pid=8.

Hickey et al., "Pharmacokinetics of oral vitamin C", Journal of Nutritional & Environmental Medicine, vol. 17, No. 3, pp. 169-177 (2008).

LivOn Labs, catalog, "Lypo-Spheric™ Vitamin C—many times more powerful than all other oral forms of Vitamin C", 2 pages, accessed online on Aug. 10, 2010 from http://www.livonlabs.com/cgi-bin/start.cgi/lypo-spheric/LSC30.html.

Organic Pharmacy, catalog, "Lipoflow, Liposomes in Action™, Liposomal Vitamin C (Heat Sensitive)", 4 pages, accessed online on Aug. 6, 2010 from http://organicpharmacy.org/products/Liposomal.Vitamin.C..(Heat.Sensitive)/SKU:LF-LIPOC4.

International Search Report from related PCT Patent Application No. PCT/US2011/023631 dated Feb. 22, 2012.

\* cited by examiner

METHOD OF MAKING LIPOSOMES, LIPOSOME COMPOSITIONS MADE BY THE METHODS, AND METHODS OF USING THE SAME

CROSS-REFERENCE TO RELATED APPLICATIONS

This applications claims the benefit of provisional application Ser. No. 61/430,024 filed Jan. 5, 2011, incorporated by reference herein in.

TECHNICAL FIELD

The subject matter described herein relates to methods for preparing liposomes, which comprise an active agent or desired compounds in liposome-entrapped form, and to methods of using the liposome compositions.

BACKGROUND

Liposomes are spherical, self-enclosed vesicles composed of amphipathic lipids. They have been widely studied and have been used as vehicles for in vivo administration of agents, compositions, and compounds. A liposome comprises at least one closed lipid bilayer membrane which defines an aqueous compartment. Liposomes have long been used for drug delivery by encapsulating water soluble agents within the internal aqueous compartment and/or water insoluble agents within the lipid bilayer. Liposomes may be unilamellar, having one lipid bilayer membrane, or multilamellar, having two or more concentrically arranged bilayers.

Various methods of preparing liposomes and encapsulation of therapeutic agents therein are well documented (see, for example, U.S. Pat. Nos. 3,932,657, 4,311,712, and 5,013,556, all of which are incorporated herein by reference). Known methods include the reverse phase evaporation method as described in U.S. Pat. No. 4,235,871, which is incorporated herein by reference.

Many of the known processes for preparing pharmaceutical liposomes are less desirable for nutraceutical liposomes, which are typically intended for oral delivery, due in part to the use of non-food grade ingredients in pharmaceutical liposomal compositions. Further, many of the known processes use a heating step, e.g. heat to solubilize the lipids, which elevates the temperature of the lipid solution. Such processes may affect the performance or efficacy of the agent, compound, or composition, especially those that are sensitive to heat and/or oxidation. Accordingly, additional processes for preparing liposomes, for nutraceutical and pharmaceutical use, are needed.

BRIEF SUMMARY

The following aspects and embodiments thereof described and illustrated below are meant to be exemplary and illustrative, not limiting in scope. Other limitations of the related art will become apparent to those of skill in the art upon a reading of the specification.

In one aspect, a method of making liposomes with an entrapped agent is provided. Generally, an appropriate amount of vesicle-forming lipids are solubilized in an aqueous solvent at or about room temperature to form a lipid solution. The agent to be entrapped is separately solubilized in an aqueous solvent at or about room temperature to form an agent containing solution. The aqueous solvent for solubilizing the lipids and the agent to be entrapped may be the same or different.

In one embodiment, the aqueous solution comprises an alcohol. In another embodiment, the aqueous solution comprises ethylenediaminetetraacetic acid (EDTA).

In one embodiment, the agent-containing solution is filtered.

In other embodiments, the lipid solution and agent-containing solution are combined.

In still other embodiments, a stream of the lipid solution is injected into the agent-containing solution with mixing.

In other embodiments, the resulting solution is allowed to hydrate for a suitable period of time. In one embodiment, the solution is allowed to hydrate for at least one hour with frequent mixing. In other embodiments, additional lipid and/or a thickener is added to form a gel. In one embodiment, the additional lipid and/or a thickener is added after the hydration step. In exemplary embodiments, the agent is selected from ascorbic acid or a salt or ester thereof, GSH, and ALA.

In a further aspect, a liposome composition for the administration of an active agent, is provided. In a preferred embodiment, the liposome composition is formed by a cold process method. In embodiments, the process is carried out at room temperature, in the absence of heat, and/or in the absence of a heating step. In embodiments, the active agent is a nutraceutical, dietary supplement, or pharmaceutical agent. In further embodiments, the active agent is selected from ascorbic acid or a salt or ester thereof, GSH, and ALA.

In other embodiments, the liposomes of the liposome composition have a selected mean particle size diameter of about 200-500 nm.

In another embodiment, the liposome of the liposome composition comprise at least about 18 w/w % vesicle-forming lipids.

In another embodiment, the vesicle-forming lipids are at least about 45-50% phosphatidylcholine.

In still other embodiments, the phosphatidylcholine is derived from soy or egg. In other embodiments, the phosphatidylcholine is a high purity phosphatidylcholine. In further embodiments, the liposome composition includes thickeners and/or emulsifiers. In embodiments, the thickeners and/or emulsifiers include xanthan gum and Tween™ 80.

In another aspect, a unit dosage comprising a unit dose package and a liposome composition contained in the package is provided.

In yet another aspect, methods for treating scurvy, cardiovascular disease, cerebrovascular disease, cancer, age-related macular degeneration, cataracts, gout, heavy metal toxicity, or diabetes in a subject with ascorbic acid or a salt thereof entrapped in a liposome are provided. In an embodiment, a high dose of the liposome composition is administered.

In a further aspect, methods for treating cancer, hepatic dysfunction, malignancies, AIDS, trauma, burns, sepsis, pulmonary disease, Parkinson's disease, diabetes, Alzheimer's disease, schizophrenia, cystic fibrosis, heart attack and stroke, seizures, sickle cell anemia, bipolarism, chronic fatigue syndrome, autism, and related immunologic illnesses in a subject with GSH entrapped in a liposome are provided In an embodiment, a high dose of the liposome composition is administered.

In another aspect, a method for treating or preventing oxidative stress or damage, diabetes, liver disease, inflammation, neurodegenerative diseases such as Alzheimer's, cardiovascular disease, peripheral nerve injury, schizophrenia, obesity, cancer, and hypertension in a subject with ALA entrapped in a liposome is provided. In embodiments, a high dose of the liposome composition is administered.

In addition to the exemplary aspects and embodiments described above, further aspects and embodiments will become apparent by reference by study of the following descriptions.

DETAILED DESCRIPTION

I. Definitions

Figure 1A:
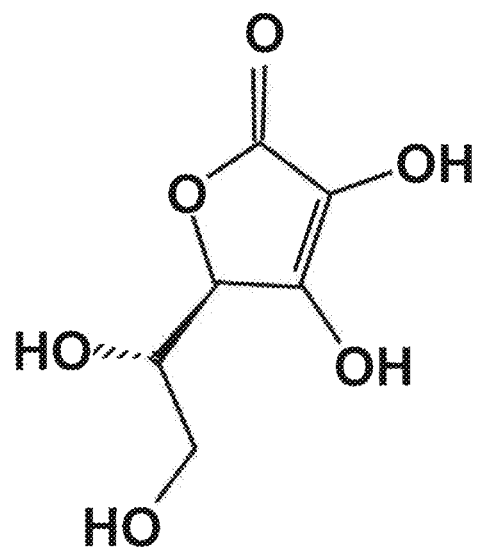
FIGS. 1A-1B are the chemical structures of L-ascorbic acid (FIG. 1A) and sodium L-ascorbate (FIG. 1B).
Figure 1B:
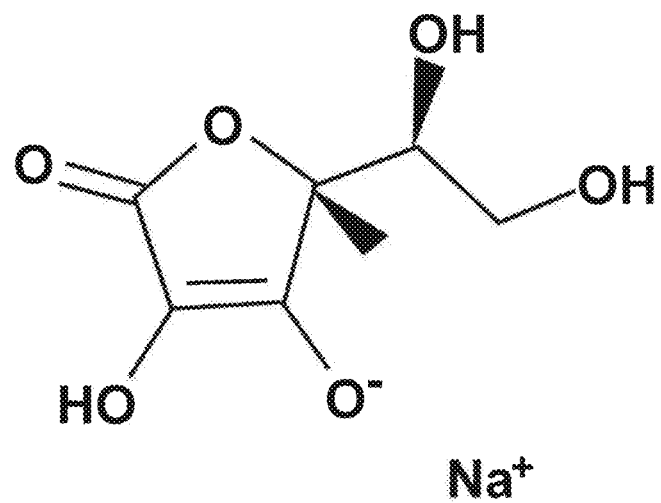

As used herein, the terms "active agent", "active compound" and "compound" refer to a composition or compound suitable for entrapment by a liposome. The terms include nutraceuticals, dietary supplements, and pharmaceuticals. Agents contemplated for use in the methods and compositions described herein are widely varied, and include agents suitable for both therapeutic applications and those for use in diagnostic applications.

"Nutraceutical" as used herein refers to a food or food product that provides health and/or medical benefits. Such benefits can be physiological, therapeutic, preventative, or diagnostic. Nutraceuticals include foods, but are not limited to, herbs, and dietary supplements.

"Dietary supplement" as used herein refers to compounds or compositions to supplement a diet and provide nutrients. Dietary supplements include, without limitation, vitamins, minerals, herbal and other botanical products, fiber, fatty acids, and amino acids or peptides.

A "pharmaceutical" or "pharmaceutical agent" as used herein refers to any chemical substance or composition intended for use in the medical diagnosis, cure, treatment or prevention of disease.

A "liposome composition" refers to liposomes which include an agent, compound, or composition at least partially entrapped in the aqueous space and/or in the lipid bilayer(s).

A "vesicle-forming lipid" refers to any lipid capable of forming part of a stable liposome composition. Such lipid typically includes one or two hydrophobic acyl hydrocarbon chains or a steroid group and may contain a chemically reactive group, such as an amine, acid, ester, aldehyde or alcohol, at its polar head group. The hydrocarbon chains are typically about 14-22 carbon atoms in length and may have varying degrees of unsaturation.

As used herein, the terms "high-dose" and "mega-dose" refer to a dose of active agent or compound greater than officially recommended doses (e.g. recommended by a government body such as the U.S. Food and Drug Administration (FDA), Department of Health in the United Kingdom, and the European Union). In embodiments, "high-dose" and "mega-dose" refer to a dose about 5-500 times greater than an officially recommended dose. In other embodiments, "high-dose" and "mega-dose" refer to a dose about 10-1000, 10-500, 10-250, 10-100, 10-50 times greater than an officially recommended dose, inclusive.

As used herein, the terms "treatment," "treating" and the like generally mean obtaining a desired pharmacological and/or physiological effect by administering a liposome composition effective to reduce the symptoms of a condition and/or lessen the severity of the condition. The effect may be prophylactic in terms of completely or partially preventing a disease or symptom thereof and/or may be therapeutic in terms of a partial or complete cure for a disease and/or an adverse effect attributable to the disease, "Treatment" as used herein covers any treatment of a disease or condition in a mammal, particularly a human, and includes: preventing the disease from occurring in a subject which may be predisposed to the disease but has not yet been diagnosed as having it; inhibiting the disease. i.e., arresting its development; or relieving the disease, i.e., causing regression of the disease. More specifically with regard to ascorbic acid, "treatment" may mean providing a therapeutically detectable and beneficial effect on a patient suffering from scurvy, cardiovascular diseases, cerebrovascular disease, cancer, age-related macular degeneration and cataracts, gout, heavy metal (such as lead and arsenic) toxicity, and diabetes.

The term "effective amount," "amount effective," or "therapeutically effective amount," when referring to the amount of the liposome entrapped agent, is defined as that amount, or dose, of the liposome composition that is sufficient for therapeutic efficacy, e.g., an amount sufficient to prevent, treat, or ameliorate the symptoms of a disease or disorder.

As used herein, "pharmaceutically acceptable" means, for example, a carrier, diluent or excipient that is compatible with the other ingredients of the formulation and generally safe for administration to a recipient thereof or that does not cause an undesired adverse physical reaction upon administration.

As used herein, "room temperature" refers to the range of temperature between about 10° C. to 37.78° C., preferably about 15.5° C. to 27° C., more preferably, about 18.3° C. to 26.7° C., inclusive. A preferred range for "room temperature" is about 20° C. to 30° C., inclusive. In specific embodiments, "room temperature" may be about 15.5° C., 18.3° C., 18.9° C., 19.4° C., 20° C., 20.6° C., 21.1° C., 21.7° C., 22.2° C., 22.8° C., 23.3° C., 23.9° C., 24.4° C., 25° C., 25.6° C., 26.1° C., 26.1° C., 26.7° C., 27.2° C., 27.8° C., 27.8° C., 28.3° C., 28.9° C., 29.4° C., 30° C., 30.6° C., 31.1° C., 31.7° C., and 32.2° C.

As used herein, "high temperature" refers to a temperature above room temperature. In non-limiting embodiments, "high temperature" refers to about 25° C. to about 60° C. In other non-limiting embodiments, "high temperature" refers to about 25° C. to about 50° C. In specific non-limiting embodiments, "high temperature" may refer to 40° C. or 50° C.

The compositions described herein can be administered alone or as admixtures with conventional excipients, for example, pharmaceutically, or physiologically, acceptable organic, or inorganic carrier substances suitable for oral, enteral or parenteral application which do not deleteriously react with the compositions employed in the method. Suitable pharmaceutically acceptable carriers include water, salt solutions (such as Ringer's solution), alcohols, oils, gelatins and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances which do not deleteriously react with the compositions employed in the methods of the invention. The preparations can also be combined, when desired, with other active substances to reduce metabolic degradation.

As used herein, "subject" has its usual meaning and includes primates (e.g.; humans and nonhumans primates), experimental animals (e.g.; rodents such as mice and rats), farm animals (such as cows, hogs, sheep and horses), and domestic animals (such as dogs and cats). With regard to liposome compositions including entrapped vitamin C, "subject" generally refers to animals that cannot synthesize ascorbic acid. Mammals that cannot synthesize ascorbate includes the Haplorrhini suborder of primates (including humans, monkeys and apes).

"Vitamin C" as used herein refers both to L-ascorbic acid and L-ascorbate, as well as to a mineral salt of ascorbic acid, or an ester of ascorbic acid.

"GSH" as used herein refers to glutathione, (2S)-2-amino-4-{[(1R)-1-[(carboxymethyl)carbamoyl]-2-sulfanylethyl]carbamoyl}butanoic acid.

"ALA" as used herein refers to alpha lipoic acid, the racemic mixture of two enantiomers R-(+)-lipoic acid (RLA) and S-(−)-lipoic acid (SLA), the active enantiomer RLA or a mineral salt of ALA.

"ATP" as used herein refers to Adenosine-5'-triphosphate, as well as to a mineral salt of ATP.

As used herein "associated with" simply means both circumstances exist and should not be interpreted as meaning one necessarily is causally linked to the other.

II. Method for Preparing Liposome Compositions

Typical methods of preparing liposomes involve heating the lipids or liposome composition during at least one step, and generally two steps, in the methods. First, it is common to heat to a high temperature the lipid-solvent composition, to facilitate solubility of the lipid in the solvent. The lipids for manufacturing liposome composition are commonly supplied as granules or as chunks of waxy material, and heat applied to the solvent is generally required to solubilize the lipids. Second, the conventional methods of liposome preparation require for encapsulation of the active agent and/or for sizing of the liposomes, a step of homogenization, sonication, or microfluidization. During homogenization (or sonication or microfluidization, as the case may be), the lipid-active agent composition is forced through an interaction chamber of the homogenizer at a high velocity, which generates heat and results in heating the lipid-active agent mixture to high temperatures. Although the composition cools down to a lower temperature once it is out of the homogenizer chamber, the bulk of the composition remains at an elevated temperature for an extended period of time after homogenization. Many active agents, lipids and compounds, including vitamins and other nutritional supplements like vitamin C, glutathiones and ALA, are sensitive to oxidation, which accelerates at high temperatures. Vitamin C, for example, is sensitive to heat, light, and oxygen, and therefore degrades quickly at the high temperatures that result from homogenization and heating during liposome encapsulation. As can be appreciated, methods of preparing liposome entrapped agents that utilize heat can degrade much of the agent in the process.

In one embodiment, the present cold process method solves this problem by providing a single step formation of small-sized liposomes at or near room-temperature (about 20-25° C.) and/or in the absence of heat. In a preferred embodiment, "cold process" refers to a method of forming liposomes in the absence of heat and/or a heating step. In another embodiment, "cold process" refers to a method of forming liposomes at or near room temperature. In this embodiment, "cold process" is synonymous with "room temperature". In other embodiments, the present method involves preparing liposomes without heat. In another embodiment, the present method involves preparing liposomes without a heating step such as heating one or more of the solvents.

This one-step process does not involve or require any further processing steps (such as homogenization or sonication or microfluidization) to encapsulate the active agent in a liposome vesicle or to size the liposomes. Therefore, the agent in the liposome compositions made via the cold process described herein has significantly less degradation and/or loss of activity when compared to agents entrapped in liposomes prepared in accord with traditional methods of forming liposome compositions.

In the cold process, the lipids are preferably completely, or mostly, solubilized in an aqueous solvent or in a solvent miscible with water, such as most alcohols. Where the liposome composition is for oral administration, the aqueous solvent is preferably one that is suitable for ingestion. In embodiments where the solvent in the cold process is an alcohol, it preferred that the final alcohol content in the final product is less than about 10-12 weight percent, based on the weight of the final product. Although alcohol is not essential to form a stable liposome product, it does appear to be helpful for making a translucent gel. Alcohol further has the benefit of serving as an effective preservative. The use of alcohol may also be helpful or effective for forming small liposomes in the size range of about 200-500 nm. Other aqueous solvents are suitable and known to those of skill in the art. However, some solvents may result in a more turbid appearance than compositions made with alcohol, In the subject cold process, lipid dissolution in alcohol can be carried out, in some embodiments, at an elevated (above room temperature) to speed up solubilization of the lipids in the solvent. However, if heat is applied to solubilize the lipid, the lipid solution is then cooled (e.g. by normal means or by use of a heat-exchanger for large scale processes) to a lower temperature (e.g. room temperature) prior to hydration with an aqueous solution of active agent. This process is fundamentally different than "typical" liposome production processes such as that described above, where both the lipids and the active agent (solutions) are heated.

With respect to the solution of active agent, in one embodiment an aqueous solution comprising the active agent is prepared, at room temperature. If desired, other compounds can be included, such as ethylenediaminetetraacetic acid (EDTA) to improve solution characteristics or enhance solubility of the active agent in water. The water may be purified by any suitable means including, but not limited to, reverse osmosis, deionization, and filtration. Once solubilized, the solution containing the agent may further be filtered to remove contaminants. One suitable filter is a 0.2 μm membrane such as the 0.2 μm Mini Capsule Sterile Filter available from Pall Life Sciences. It will be appreciated that the size of the membrane may be adjusted according to the size of contaminants that are to be removed from the solution. Selection of a suitable size filter is well within the skill of one in the art. Suitable filter sizes include, without limitation, 0.5 μm, 0.4 μm, 0.45 μm, 0.3 μm, 0.2 μm, 0.15 μm, and 0.1 μm.

Next in the cold process, the lipid solution is added to the active-agent aqueous solution, such as by injecting the lipid solution or pouring the lipid solution into the active agent aqueous solution, optionally with agitation. Agitation may be provided by any suitable means including mechanical vortexing such as with a mixer, and hand mixing or stirring. After the lipid solution has been added to the agent aqueous solution, lipid hydration should be allowed to continue for at least about ½ or one hour with frequent mixing. At the end of the process, the resulting lipid composition is preferably a smooth fluid.

In order to make the liposome composition palatable and easy to handle, in one embodiment, the liposomal nutritional supplement or composition is formulated to have the consistency of a gel. In one embodiment, additional lipid is added to the composition to increase the viscosity of the liposome composition to a gel-like viscosity. In another embodiment, a thickener and/or emulsifier is added to make the composition a gel, with or without adding more lipid. Suitable thickeners and/or emulsifiers include xanthan gum, locust bean gum, Tween™ 80 (Polysorbate 80), Tween™ 20 (Polysorbate 20), Tween™ 40 (Polysorbate 40), Tween™ 60 (Polysorbate 60), lecithin, emulsifying wax, cetearyl alcohol, and ceteareth 20. Further suitable thickening agents are described on the web at en.wikipedia.org/wiki/Category: Edible_thickening_agents. The use of thickeners and/or emulsifiers may be used to reduce the amount of lipid needed to make a gel. Alternatively, the amount of lipid can be increased up to 30-35% from the amount necessary to form liposomes in order to make a liposome composition with a gel-like consistency, in the absence of thickeners and/or emulsifiers. Using excess lipid to make a gel composition offers a higher encapsulation efficiency for the active agent. A combination of additional lipid(s) and thickener and/or emulsifier may be used to create the gel composition. Addition of excess lipid, thickener, and/or emulsifiers may also have the benefit of making the gel more palatable for oral consumption. Such a composition may have a honey-like color rather than the orange or brownish color of liposome compositions formed by other methods. Compositions formed by the present method are also preferably partially or wholly transparent.

An exemplary liposome formulation for sodium ascorbate as the active agent is provided in Table 1. It will be appreciated that the formulation in Table 1 is provided for example only. The formulation is non-limiting and may include other ingredients and different ranges. It will be appreciated that the percent of active agent may vary based on the properties of the active agent.

TABLE 1

Exemplary liposome formulation

|  | w/w % | Range of Variation (wt %) |
|---|---|---|
| Lipid[1] | 18.73 | 10-30 |
| Sodium Ascorbate (Vitamin C) | 22.00 | 5-25 |
| water | 47.5 | qs to 100 |
| Alcohol (200 proof) | 11.00 | 0-15 |
| Xanthan gum | 0.42 | 0-2 |
| Tween ™ 80 | 0.26 | 0-2 |
| EDTA | 0.005 | 0.005-0.1 |

[1]At least 45-50% preferably being PC such as Phospholipon 50IP, a non-GMO PC, or Alcolec PC 50.

III. Liposome Composition

In one aspect, the agent, composition, or compound is entrapped in a liposome.

The active agent, compound, or composition may be encapsulated in a variety of liposome compositions. It is well within the knowledge of one of skill in the art to select the constituents and ratios of the constituents of the liposome composition depending on considerations such as the form of the agent (e.g. ascorbic acid, ascorbate, mineral salt, ester, etc. for vitamin C) and the method of administration, Lipids for use in forming a liposome composition include vesicle-forming lipids having two hydrocarbon chains, typically acyl chains, and a polar head group. Included in this class are the phospholipids, such as phosphatidylcholine (PC), phosphatidylethanolamine (PE), phosphatidic acid (PA), phosphatidylinositol (PI), and sphingomyelin (SM), where the two hydrocarbon chains are typically between about 14-22 carbon atoms in length, and have varying degrees of unsaturation. In a preferred embodiment, the lipid is a relatively unsaturated phospholipid (having one, two or three double bonds in the hydrocarbon chain). In a particularly preferred embodiment, the lipid is a phosphatidylcholine. Phosphatidylcholine is a phospholipid that incorporates choline as a headgroup and combines a glycerophosphoric acid with two fatty acids. PC is a major component of biological membranes and may be extracted from available sources such as egg yolk or soy beans by known methods. In one embodiment, the lipid is phosphatidylcholine derived from soy. In another embodiment, the lipid is phosphatidylcholine derived from egg yolk. Suitable phosphatidylcholine lipids include, but are not limited to, Phospholipon 50IP and Alcolec PC 50 available from American Lecithin Company (Oxford, Conn.). It will be appreciated that more than one type of lipid may be used in preparing the liposome composition. The selection of lipids and proportions can be varied to achieve a desired degree of fluidity or rigidity, to control stability, and/or to control the rate of release of the entrapped agent. Where more than one type of lipid is used in preparing the liposome composition, a suitable amount of the relatively unsaturated lipid (such as PC) should be used in order to form stable liposomes. In one embodiment, at least 45-50 mol % of the lipids used in the formulation are PC. The liposomes may also include lipids derivatized with a hydrophilic polymer such as polyethylene glycol (PEG). Suitable hydrophilic polymers include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide, and hydrophilic peptide sequences. Methods of preparing lipids derivatized with hydrophilic polymers are known (see e.g. U.S. Pat. No, 5,395,619, which is incorporated herein by reference).

The liposomes may further be administered in a capsule, such as a gelatin capsule or a soft gel capsule as known in the art.

As described in Examples 4-5 and 9, the present liposome composition is highly stable. It has further been shown that the present liposome composition is highly stable when stored at high temperatures (temperatures above room temperature). "Stability" as used herein refers to a formulation which retains a majority of the entrapped agent during and after storage. In non-limiting embodiments, the liposomes retain stability after storage for at least about six months or a year. In other non-limiting embodiments, the liposomes retain stability after storage for at least about 1-12 months inclusive. In other non-limiting embodiments, at least about 1, 2, 3, 4, 5, 6, 9 months or more. In embodiments, at least or more than about 65-100%, inclusive, of the entrapped agent is retained within the liposomes after the storage. Preferably, at least or more than about 65%, 70%, 80%, 90%, 95%, 97%, 98%, 99%, or 100% of the entrapped agent is retained within the liposomes after the storage. Where the liposomes are stored at a high temperature (above room temperature and e.g. 25-60° C., preferably at about 50° C.), preferably at least about 65% of the entrapped agent is retained within the liposomes after the storage.

In an embodiment, the present liposomes have a particle size of 200-600 nm, preferably about 200-500 nm or about 300-500 nm. As seen in Example 3, the liposomes formed by the cold process have a substantially smaller particle size than commercially available oral liposomes. Liposomes with a smaller particle size are generally more palatable for oral administration, Therefore, the liposomes formed by the present methods are more palatable than commercially available oral liposomes. In one embodiment, the liposomes formed by the present method have an average size distribution that is 25-75% smaller than liposomes formed by other methods such as the commercially available liposomes. In non-limiting embodiments, the present liposomes have an average size distribution that is 25%, 35%, 40%, 45%, 60%, 65% or 75% less than liposomes formed by other methods such as commercially available liposomes, IV. Entrapped Agents Agents, compounds, and compositions contemplated for use in the methods and liposome compositions are widely varied and include nutraceutical agents, including dietary supplements, and pharmaceutical agents.

A. Nutraceutical Agents

1. Ascorbic Acid and Salts Thereof

Ascorbic acid is a water-soluble sugar acid with antioxidant properties. Because of its antioxidant properties, ascorbic acid and its sodium, potassium, and calcium salts are commonly used as food additives. Similarly, fat-soluble esters of ascorbic acid with long-chain fatty acids (such as ascorbyl palmitate or ascorbyl stearate) are commonly used to prevent fats from oxidizing. The L-enantiomer of ascorbic acid (known as Vitamin C or L-ascorbic acid, with the salt being L-ascorbate) is an essential nutrient for humans and some other mammals as they are unable to make ascorbic acid. Deficiency of Vitamin C causes scurvy in humans. Vitamin C is also required for the synthesis of collagen, L-carnitine, and certain neurotransmitters such as norepinephrine. Vitamin C is further involved in protein metabolism and is a highly effective antioxidant.

Vitamin C has long been available as a nutritional supplement as many people do not obtain enough vitamin C in their diet. The National Health and Nutrition Examination Survey data from 1999-2000 showed that approximately 35% of adults take a multivitamin supplement, which typically includes vitamin C. The data also showed that 12% of adults take a separate vitamin C supplement (Radimer, et al., Am. J. Epidemiol., (2004.) 160:339-49). Vitamin C is the most widely taken dietary supplement. Vitamin C is available for oral use in tablet form and by intravenous administration. It is available for oral use in caplets, tablets, capsules, drink mix packets, in multi-vitamin formulations, in multiple antioxidant formulations, and as a crystalline powder. However, oral administration is generally limited to about 2-3 grams/day due to bowel irritation and diarrhea that can accompany larger doses. It has been found that vitamin C may cause diarrhea when taken in doses larger than the bowel tolerance level (Cathcart, Medical Hypothesis (1981), 7:1359-1376). Bowel tolerance of vitamin C varies from individual to individual and can range from 5 mg per day to thousands of mg per day.

The use of vitamin C, including high or mega doses, has long been advocated for the treatment of a variety of diseases and disorders including cardiovascular diseases, cancer, cataracts, gout, and heavy metal (such as lead and arsenic) toxicity. High or mega-doses of vitamin C have traditionally be given intravenously to avoid the side effects of oral doses and to increase plasma levels beyond those typically achieved with oral administration. Intestinal absorption of vitamin C is generally thought to be regulated by at least one specific dose-dependent active transporter, thus limiting the amount of vitamin C that is absorbed (Jacob et al., Nutr. Olin. Care, (2002), 5:66-74). Pharmacokinetic modeling predicted that doses as high as 3 g ascorbic acid taken orally every 4 hours would produce peak plasma concentrations of only 220 micromol/L (Padayatty, et al., Ann. Intern. Med. (2004) 140:533-7).

To increase absorption and reduce the side effects of oral administration, vitamin C has been encapsulated in liposomes for oral administration. Lipoflow provides a liposomal vitamin C for disorders of lipid metabolism and atherosclerosis. Each tablespoon of the supplement contains 1,000 mg of vitamin C encapsulated in essential phospholipids from soy lecithin. LivOn Laboratories offers a supplement that contains liposomes of 1,000 mg of vitamin C encapsulated in 1,000 mg of essential phospholipids. Existing liposomal vitamin C formulations comprise large diameter liposomes (about 800-1000 nm), which makes oral administration less palatable. Because of the liposome size, the existing formulations are turbid. Therefore, there is a need for more palatable and stable oral liposome formulation.

In one aspect, a nutritional supplement or composition comprising L-ascorbic acid, L-ascorbate, a mineral salt of ascorbic acid, or an ester of ascorbic acid is provided in a liposome composition. In one embodiment, the nutritional supplement or composition comprises an alkali metal salt of L-ascorbic acid. Suitable mineral salts include, but are not limited to, sodium ascorbate, calcium ascorbate, potassium ascorbate, magnesium ascorbate, zinc ascorbate, molybdenum ascorbate, chromium ascorbate, and manganese ascorbate. Since the mineral salts are buffered, they may be less irritating than ascorbic acid when ingested. It will be appreciated that a combination of mineral salts of ascorbic acid may be used. This may be especially important where a high or mega dose is administered in order to keep the recommended dietary intake for the cation of the mineral salt within or near recommended dietary guidelines. In another embodiment, the nutritional supplement or composition includes ascorbic acid esterified to a saturated fatty acid to produce a fat-soluble form. One suitable fatty acid is palmitic acid to form ascorbyl palmitate. The L-ascorbic acid, mineral salt or ester thereof is preferably entrapped in a liposome.

a. High-Dose

In another aspect, a high dose or mega dose of a liposome composition containing a nutritional supplement or composition comprising L-ascorbic acid, a mineral salt of ascorbic acid, or an ester of ascorbic acid is provided. The Dietary Reference Intake developed by the Institute of Medicine's Food and Nutrition Board for Vitamin C ranges from 45 to 120 mg/day for adolescent and adult individuals. Smokers are recommended to ingest an additional 35 mg/day. The FDA updated the Recommended Daily Intake (RDI) to 60 mg per day in 2009 (www.fda.gov). Generally, "high-dose" and "mega-dose" refer to a dose of between about 100-10,000 mg per day. A "high-dose" and "mega-dose" may also be the "bowel tolerance dosage", which is a dose just below the dose where a subject experiences diarrhea (see Cathcart, Medical Hypotheses, 7:1359-1376, 1981 for an exemplary method of determining the "bowel tolerance dosage", incorporated herein by reference). In a preferred embodiment, "mega-dose" refers to a dose of ascorbic acid or a salt thereof at or greater than 2000 mg/day. In another embodiment, the high-dose of the liposome composition comprising vitamin C includes a dose of vitamin C above the recommended intake as set by the National Academy of Sciences (90 mg/day in 2000), the Food and Nutrition Board (75-120 mg/day), the USDA, or other governmental regulatory body. In embodiments, a dose of about 100-10,000 mg is administered per day. In other embodiments, the dose is about 200-2,000 mg/day, 200-5,000 mg/day, 200-10,000 mg/day, 400-10,000 mg/day, 400-8,000 mg/day, 400-6,000 mg/day, 400-5,000 mg/day, 400-4,000 mg/day, 400-3,000 mg/day, 400-2,000 mg/day, 500-10,000 mg/day, 500-8,000 mg/day, 500-6,000 mg/day, 500-5,000 mg/day, 500-4,000 mg/day, 500-3,000 mg/day, 500-2,000 mg/day, 500-1000 mg/day, 1000-10,000 mg/day, 1000-8,000 mg/day, 1,000-6,000 mg/day, 1,000-5,000 mg/day, 1,000-4,000 mg/day, 1,000-2,000 mg/day, 2,000-10,000 mg/day, 2,000-6,000 mg/day, 2,000-5,000 mg/day, 2,000-4,000 mg/day, 4,000-10,000 mg/day, 4,000-8,000 mg/day, 4,000-6,000 mg/day, 4,000-5,000 mg/day, or 5,000-10,000 mg/day, inclusive. The dose should be below the LD50 for humans. The oral LD50 is 11,900 mg per kg in rat populations (MSDS Data Sheet for ascorbic acid) although is it is lower for mice (3367 mg/kg). It will be appreciated that the dose may be administered once or several times per day. Preferably, doses above 1000 mg that are administered more than once per day are administered at least 30 minutes apart, Although some studies suggest that oral vitamin C levels reach blood serum saturation at a dose of about 200-240 mg, these studies were generally based on a measurement of blood plasma levels after 12 or 24 hours, Since, vitamin C has a half-life of 30 minutes, the actual blood serum saturation should be much higher making high or mega-doses of vitamin C feasible. A 1991 study conducted at the USDA Human Nutrition Research Center found that ocular levels of vitamin C were much higher among older adults who consumed 2000 mg/day of vitamin C as compared to those who consumed 148 mg/day, which shows higher doses are absorbed and distributed in tissue (Taylor et al., Current Eye Research, 1991, 10(8):751-759). Approximately 70-90% of oral vitamin C is absorbed at doses of 30-180 mg/day (Vitamin C Fact Sheet at ods.od.nih.gov). However the absorption decreases as the dose increases. High levels of vitamin C are maintained in cells and tissues with the highest concentrations found in leukocytes, the eyes, adrenal glands, pituitary gland, and the brain (Vitamin C Fact Sheet at ods.od.nih.gov).

Because vitamin C is water soluble (33 g/100 mL), it is not stored in the body and vitamin C toxicity is very rare even at high or mega-doses. When taken in large doses, vitamin C may cause indigestion, particularly when taken on an empty stomach, and diarrhea (news-medical.net/Vitamin-C-Side-Effects.aspx). In a 1936 trial, doses up to 6 grams of ascorbic acid were given to 29 infants, 93 children of preschool and school age, and 20 adults for more than 1400 days. At the higher doses, toxic manifestations were observed in five adults and four infants. The signs and symptoms in adults were nausea, vomiting, diarrhea, flushing of the face, headache, fatigue and disturbed sleep. The main toxic reactions in the infants were skin rashes (Widenbauer, Klin. Wschr, 33:1157, 1936). Another study found doses up to 10,000 mg of vitamin C consumed daily for up to three years safe (Bendich, et al., J. Am. College Nutr., 1995, 14(2):124-136)

b. Liposome Composition

The nutritional supplement or composition may be encapsulated in a variety of liposome compositions. It is well within the knowledge of one of skill in the art to select the constituents and ratios of the constituents of the liposome composition depending on considerations such as the form of the vitamin C (ascorbic acid, ascorbate, mineral salt, ester, etc.) and the method of administration. In one embodiment, the liposome encapsulated agent is L-ascorbic acid, mineral salt or ester thereof.

Figure 3:
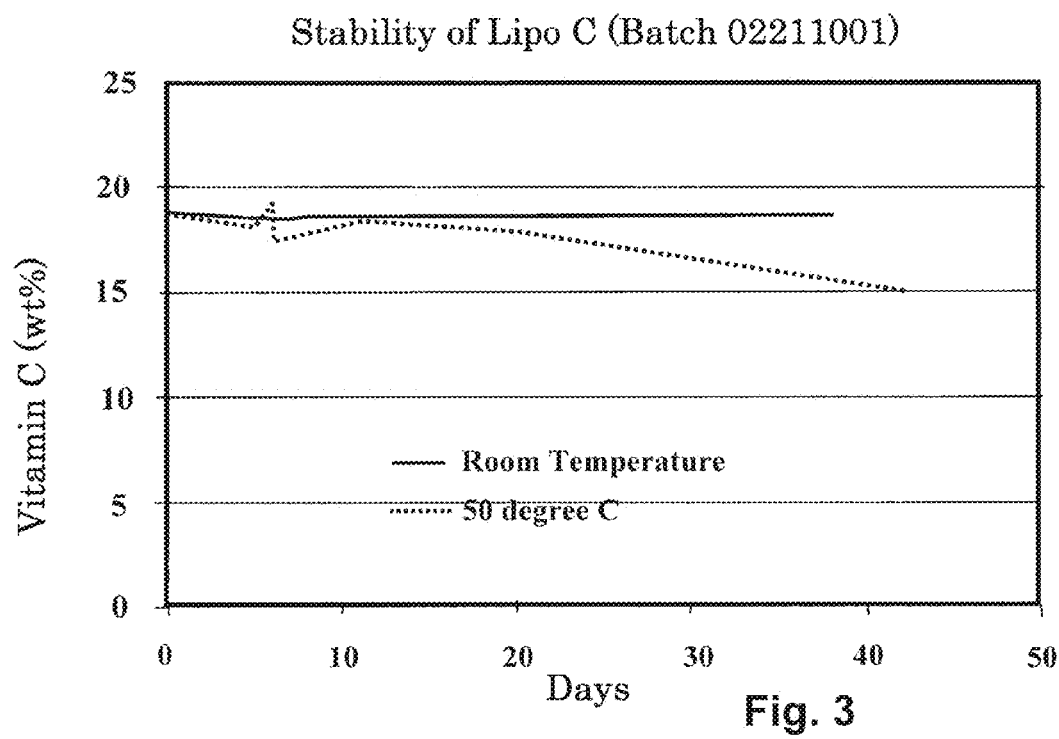
FIG. 3 shows the stability of sodium ascorbate entrapped in liposomes stored at room temperature (♦) and at 50° C. (■) as the wt % of vitamin C over time (days).

The present liposome composition is proven to be highly stable. It has further been proven that the present liposome composition is highly stable when stored at high temperatures. This is especially beneficial since vitamin C is sensitive to heat, which accelerates oxidation of the molecule. "Stability" as used herein refers to a formulation which retains a majority of vitamin C. Preferably, at least or more than about 65%, 70%, 80%, 90%, 95%, 97%, 98%, 99%, or 100% of the vitamin C is retained within the liposomes. Where the liposomes are stored at a high temperature (e.g. at about 50° C.), preferably at least about 65% of the vitamin C is retained within the liposomes. An exemplary liposome composition was prepared whereby sodium ascorbate (18.4 wt %) was encapsulated in liposomes comprising Alcolec PC 50 lipids (see Examples 1 and 4). As described in Example 4, the liposome composition was stored in 2 mL vials sealed under $N_2$ at room temperature (25° C.) or at high temperatures (50° C.). On days 4, 5, 7 (two vials were measured), 8, and 38, the weight percent of ascorbic acid was measured by HPLC. As seen in FIG. 3, the ascorbic acid weight percent for the vials stored at room temperature was highly stable over the entire period. At day 38, 99.8% of the ascorbic acid that was present at day 4 was still present in the sample showing that there is little or no vitamin C degradation after storage at 25° C. for 38 days. Preferably, a majority of the vitamin C is retained within the liposomes for a period of at least about one week, two weeks, three weeks, one month, two months, three months, six months, or a year.

Figure 6:
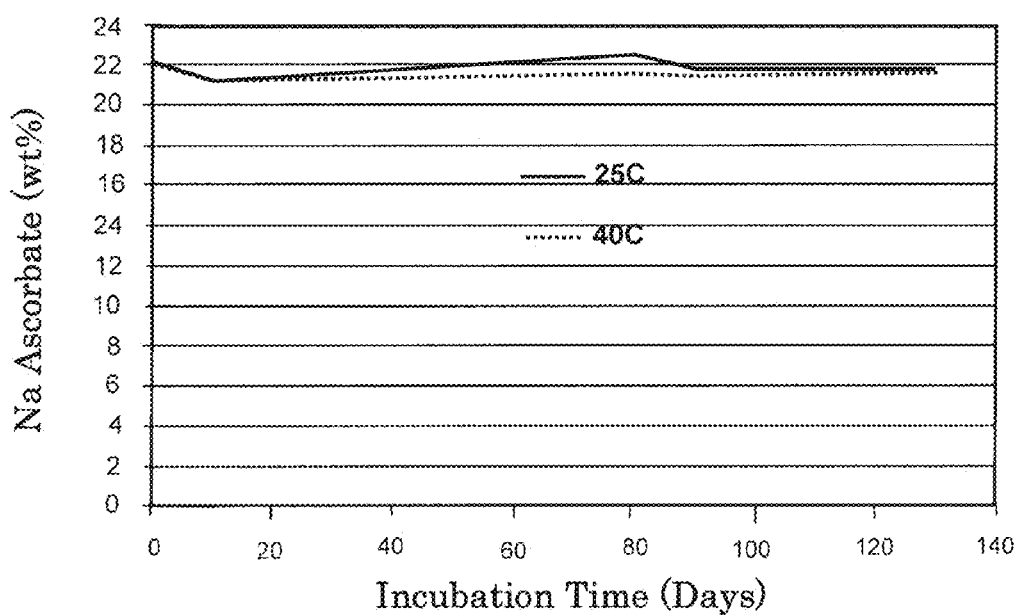
FIG. 6 shows the stability of liposomes prepared by an embodiment of the present method stored in vials at 25° C. (♦) and 40° C. as the wt % of sodium ascorbate.

Even at high temperatures, the vitamin C content in the liposome composition was highly stable. As seen in FIG. 3, after 20 days at 50° C., about 96% of the starting amount of vitamin C remained stable. Even after 42 days, 80.8% of the weight percent of ascorbic acid was still present in the liposome composition. Further, as seen in FIG. 6, the wt % of entrapped sodium ascorbate was stable after storage at room temperature (25° C.) and at high temperature (40° C.) even after 120 days.

Figure 4:
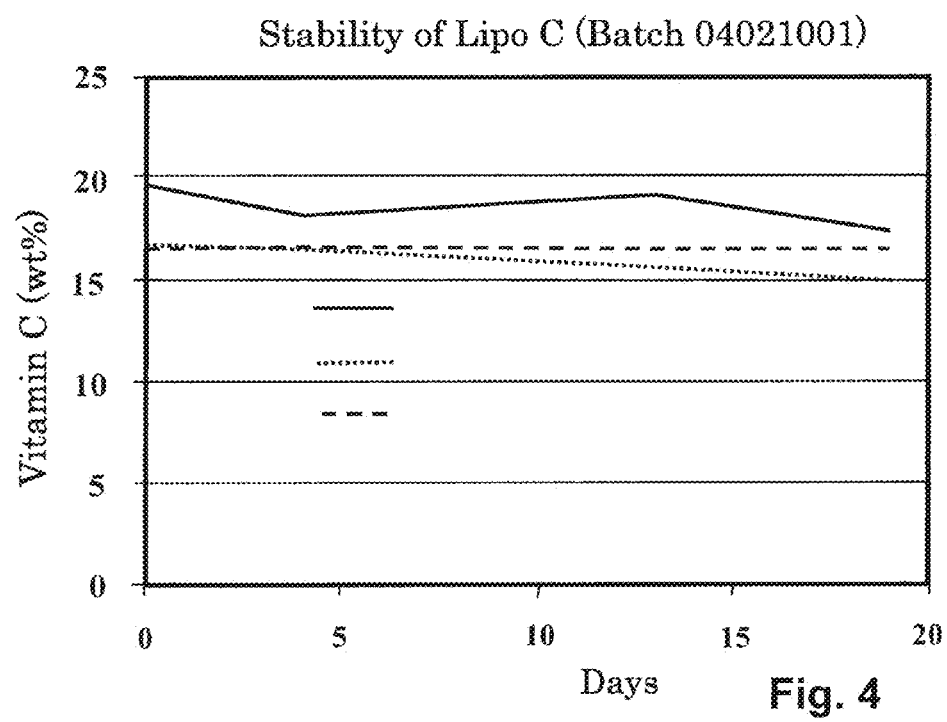
FIG. 4 shows the stability of liposomes prepared by an embodiment of the present method stored in vials at 50° C. (■), commercially available sodium ascorbate entrapped in liposomes (LivOn Lypo-Spheric™ Vitamin C) stored in vials at 50° C. (♦), and commercially available sodium ascorbate entrapped in liposomes (LivOn Lypo-Spheric™ Vitamin C) stored in the original packaging at 50° C. (▲) as the wt % of vitamin C over 19 days.

This stability was at least comparable to presently available vitamin C compositions. As described in Example 5, the storage stability of the present liposome composition prepared with non-GMO lipids as described in Example 1 was compared to a vitamin C liposome formulation commercially available from LivOn Laboratories (Lypo-Spheric™ Vitamin C liposomes). The present liposome composition and the Lypo-Spheric™ Vitamin C liposomes were stored in 2 mL vials sealed under $N_2$ at a high temperature (50° C.). As a comparison, the stability of the Lypo-Spheric™ Vitamin C liposomes was also monitored for liposome stability when stored in the original packaging. The weight percent of ascorbic acid was measured at days 0, 4, 13, and 19. As seen in FIG. 4, after 4 days, about 92% of the starting amount of vitamin C remained stable, after 13 days, about 97% of the starting amount of vitamin C remained stable, and after 19 days, about 89% of the liposome remained stable. This was comparable to the LypoSpheric™ Vitamin C liposomes which retained about 99-90% of the vitamin C in liposomes over 19 days.

As seen in FIG. 4, the stability of the Lypo-Spheric™ Vitamin C liposomes was greater when the liposomes were stored in the original packaging (sealed under $N_2$) with 99.5% of the weight percent of ascorbic acid remaining after 19 days. Since stability of the present liposome composition is comparable to the Lypo-Spheric™ Vitamin C liposomes, it is likely that storage of the present liposomes in the same sealed, $N_2$ flushed packaging will result in similar stability.

Figure 5:
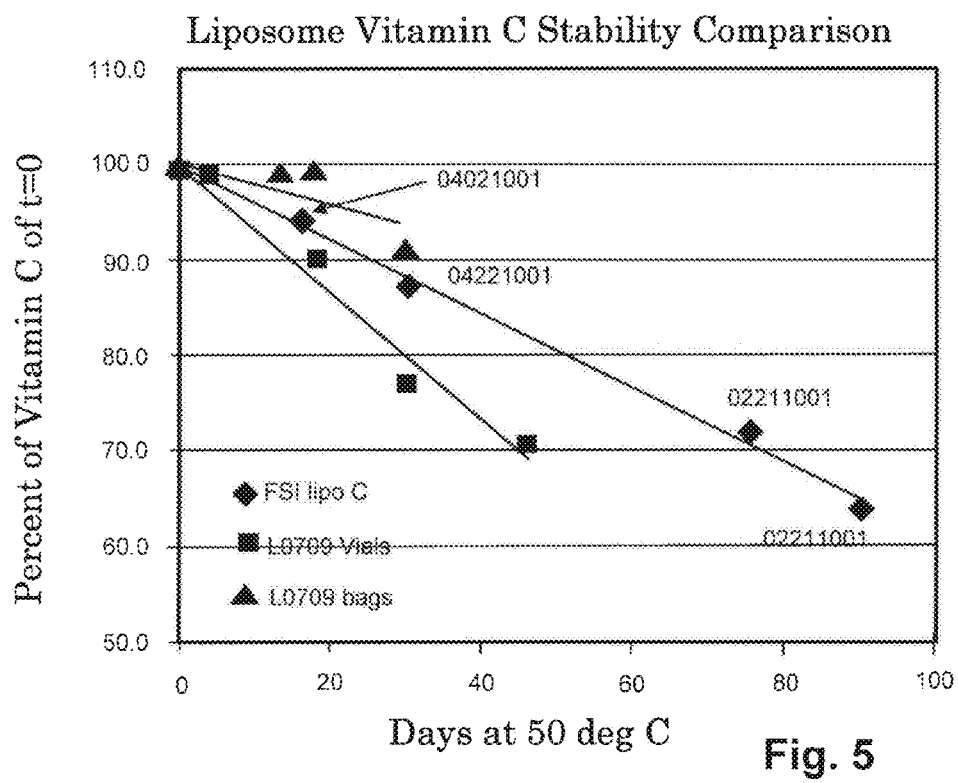
FIG. 5 shows the stability of liposomes prepared by an embodiment of the present method stored in vials at 50° C. (♦), commercially available sodium ascorbate entrapped in liposomes (LivOn Lypo-Spheric™ Vitamin C) stored in vials at 50° C. (■), and commercially available sodium ascorbate entrapped in liposomes (LivOn Lypo-Spheric™ Vitamin C) stored in the original packaging at 50° C. (▲) as the wt % of vitamin C over 90 days.

FIG. 5 is a graph comparing the stability of the liposomes over 90 days for different lots of the present liposomes and Lypo-Spheric™ Vitamin C liposomes. As seen from the figure about 65% of the starting ascorbate remained active after three months at 50° C. This is superior stability as compared to the Lypo-Spheric™ Vitamin C liposomes. As seen in the figure, the ascorbate in the Lypo-Spheric™ Vitamin C liposomes trended down much faster than the present liposomes.

c. Methods of Use

In another aspect, methods of using liposome compositions prepared in accord with the process described herein are contemplated. Of course, the method of use or method of treatment depends on the entrapped compound. Hereinbelow, several examples for method of use are set forth, but a skilled artisan will appreciate that the examples are merely exemplary.

In one aspect, a method for treating or preventing scurvy, cardiovascular disease, cerebrovascular diseases, cancer, age-related macular degeneration and cataracts, gout, heavy metal toxicity (such as lead, arsenic, cadmium, copper, and mercury), and diabetes by administering a dose of liposome entrapped vitamin C is provided. In one embodiment, the dose is a high or mega-dose of liposome entrapped vitamin C. Vitamin C is an anti-oxidant and a cofactor in at least eight enzymatic reactions. Vitamin C is also required for the synthesis of collagen, an important structural component of blood vessels, ligaments, and bone. Vitamin C also plays a role in the synthesis of norephinephrine, a neurotransmitter. Vitamin C is further involved in the metabolism of cholesterol to bile acids, which may impact blood cholesterol levels (Simon et al., Arch. Intern. Med., 2000, 160(7):931-936). Several individuals and organizations advocate large doses of vitamin C (Linus Pauling Institute at lpi.oregonstate.edu/infocenter/vitamins/vitaminC/index.html) for the treatment of a variety of disorders and diseases. In addition to treating and preventing scurvy, research indicates vitamin C is effective for treatment or prevention of cardiovascular disease, cerebrovascular disease, cancer, age-related macular degeneration and cataracts, gout, heavy metal toxicity (including lead, copper (Mahajan et al., Asian J of Microbiology, Biotech. & Env. Sci., 2001, 3(1-2):95-100), mercury (Mahajan et al.), cadmium (Borane, et al., J. Aquatic Biology, 2006, 21(2):244-248), and arsenic (Karasawas, et al., Blood, 2005, 105(10):4004-4012)), and diabetes.

Cardiovascular Disease

Cardiovascular disease is a class of diseases that involves the heart or blood vessels. Cardiovascular disease includes, but is not limited to, high blood pressure, coronary heart disease, including myocardial infarction and angina pectoris, stroke and heart failure. Coronary heart disease is caused by atherosclerosis, which is a narrowing of the coronary arteries due to a build-up of fatty materials such as cholesterol. Coronary heart disease is the single leading cause of death in the United States (American heart.org).

Vitamin C has been shown to reduce monocyte adherence to the endothelium, improve endothelium-dependent nitric oxide production and vasodilation, and reduce vascular smooth-muscle cell apoptosis (Honarbakhsh, et al., Br. J. Nutr., 2008, 1-19). Randomized, double-blind, placebo-controlled studies have shown that treatment with vitamin C results in improved vasodilation in subjects suffering from coronary heart disease as well as subjects suffering from angina pectoris, congestive heart failure, high cholesterol, and high blood pressure (Gokce, Circulation, 1999, 99(25): 3234-3240; Versari, et al., Br. J. Pharmacol., 2009, 157(4): 527-536; and Frikke-Schmidt et al., Basic Clin. Pharmacol. Toxicol., 2009, 104(6):419-433).

Several studies have shown the benefits of supplementation with vitamin C for treatment of cardiovascular disease. In a prospective study in 20,649 men and women aged 40-79 without prevalent stroke, plasma vitamin C concentrations were monitored in relation to stroke. Subjects in the top quartile of baseline plasma vitamin C concentration had a 42% lower risk for stroke than those in the bottom quartile (Myint, et al., Am. J. Cling. Nutr., 2008, 87(1):64-69). In the Linxian trial, daily vitamin C (120 mg) plus molybdenum provided for 5-6 years reduced the risk of cerebrovascular deaths by 8% during 10 years of follow-up after supplementation ceased (Qiao, et al., J. Natl. Cancer Inst., 2009, 101(7):507-518). A pooled analysis of nine studies found that people who took ≥700 mg/day of vitamin C had a 25% lower risk of coronary heart disease (Knekt, et al., Am. J. Clin. Nutr., 2004, 80(6)1508-1520), Cancer Epidemiologic evidence suggests that higher consumption of fruits and vegetables is associated with lower risk of most types of cancer, perhaps, in part, due to their high vitamin C content (Li, et al., J. Nutr., 2007,137:2171-84). Most case-control studies have found an inverse association between dietary vitamin C intake and cancers of the lung, breast, colon or rectum, stomach, oral cavity, larynx or pharynx, and esophagus (Jacob, et al., Nutr. Olin. Care. 2002, 5:66-74). Plasma concentrations of vitamin C are also lower in people with cancer than controls (Carr, et al. Am. J. Clin. Nutr., 1999, 69:1086-107), Intravenous administration of vitamin C has been shown to produce plasma concentrations as high as 26,000 micromol/L (Padayatty, et al., CMAJ 2006, 174:937-942). Concentrations of this magnitude are selectively cytotoxic to tumor cells in vitro (Li, et al., J Nutr 2007, 137:2171-84; and Shekelle, et al., Evidence Report/Technology Assessment No. 83 AHRQ Publication No. 03-E043. Rockville, Md.:

Agency for Healthcare Research and Quality, 2003). Research in mice suggests that pharmacologic doses of intravenous vitamin C shows promise in treating otherwise difficult-to-treat tumors (Chen, et al., Proc Natl Aced Sci USA 2008, 105:11105-11109). A high concentration of vitamin C may act as a pro-oxidant and generate hydrogen peroxide that has selective toxicity toward cancer cells (Chen et al, 2009; Chen, et al., Proc Natl Aced Sci USA, 2005, 102;13604-13609; and Chen et al., Proc Natl Aced Sci USA, 2007, 104:8749-8754). There are also a few case reports of patients with advanced cancers who had remarkably long survival times following administration of high-dose intravenous vitamin C (Levine, et al., Free Radic. Biol. Med., 2009, 47:27-29).

Diabetes

Diabetes mellitus is a group of diseases characterized by high blood glucose levels that results from defects in the body's ability to produce and/or use insulin. There are 23.6 million people in the United States alone that suffer from a form of diabetes including Type I, Type II, and gestational diabetes (diabetes.org).

Type 1 diabetes is usually diagnosed in children and young adults and is characterized by an inability to produce insulin. Treatment of Type I diabetes usually requires insulin therapy. A 1993 study of Type 1 patients showed that administration of intravenous vitamin C produced a bimodal plasma concentration curve for insulin (Kodama, et, al., In Vivo, 1993, 7(6A):535-542). These results suggest that vitamin C may aid in the treatment of diabetes by stimulating the insulin mechanism. Additionally, vitamin C may be used to prevent or reduce the blood vessel damage caused by diabetes in patients with poor glucose control.

Type II diabetes is the most common form of diabetes. Type II diabetes is characterized by an inability by the body to produce enough insulin or inability of the cells to effectively use insulin. A study of patients with Type II diabetes receiving 1000 mg of vitamin C supplement daily at the Yazd Diabetes Research Center showed a significant decrease in fasting blood sugar, triglyceride, low density lipoprotein, glycated hemoglobin and serum insulin levels in 42 days as compared to patients receiving 500 mg of vitamin C per day (Afkhami-Ardekani, et al., Indian J. Med. Res., 2007, 126(5):471-474). The average fasting blood glucose levels fell from 169.33 mg/dl to 144.80 mg/dl. The Average $HbA_1C$ was reduced from 8,82% to 7.66%. The average LDL was reduced from 130.95 mg/dl to 125.91 mg/dl. Insulin levels were reduced from 16.91 microunits/mL to 8.77 microunits/mL. These results show that daily consumption of at least about 1000 mg supplementary vitamin C is beneficial in decreasing blood glucose and lipids in patients with Type II diabetes.

Age-Related Macular Degeneration and Cataracts

Age-Related Macular Degeneration (AMD) and cataracts are two of the leading causes of vision loss in older individuals. AMD is a disease that affects the macula and results in a gradual loss of sharp, central vision. The wet form of AMD occurs when abnormal blood vessels behind the retina grow under the macula and cause damage to the macula. The dry form of AMD occurs when the light-sensitive cells in the macula slowly break down causing a blurring in the central vision. A cataract is a clouding that develops in the crystalline lens of the eye or its envelope. The current treatment for severe cataracts is surgery to replace the lens.

Because oxidative stress may contribute to the etiology of both AMD and cataracts, antioxidants such as vitamin C may be used to treat or prevent these diseases. Research has shown that vitamin C may slow AMD progression (Evans, Cochrane Database Syst. Rev., 2006, (2);CD000254). Further, a prospective study showed that dietary vitamin C reduced the risk of age-related cataracts in a middle-aged Japanese population of women (Yoshida, et al., Eur. J. Nutr., 2007, 46:118-124; and Rautiainen, et al., Am. J. Clin. Nutr., 2010, 19(2):487-493).

Because vitamin C is a recognized antioxidant, in one aspect, a method of treating or preventing a disease or condition with liposome entrapped vitamin C is contemplated for any disease or condition that is amenable to treatment or prevention with an antioxidant.

2. Glutathione

Glutathione (GSH) is a tripeptide that is synthesized from the amino acids cysteine, glutamic acid, and glycine. GSH contains a peptide linkage between the amine group of cysteine and the carboxyl group of the glutamate side-chain. GSH is found in bacterial and mammalian cells at one to ten millimolar concentrations, and serves as a sulfhydryl buffer that maintains the cysteine residues of cellular proteins in the reduced state (U.S. Pat. No. 7,785,900). GSH exists in two basic forms: the antioxidant or "reduced" glutathione tripeptide is generally the form referred to as "glutathione" or "GSH": the oxidized form is a sulfur-sulfur linked compound known as glutathione disulfide (GSSG). GSH is the major endogenous antioxidant produced by the cells, participating directly in the neutralization of free radicals and reactive oxygen compounds, as well as maintaining exogenous antioxidants such as vitamins C and E in their reduced (active) forms. GSH functions as an antioxidant, antitoxin and protector of red blood cells, and is extremely important to the immune system (U.S. Pat. No. RE40849). GSH neutralizes free radicals minimizing the damage they cause and is thus important for cellular homeostasis. Reduced GSH levels in mammalian cells are associated with a wide variety of pathophysiologic states, including cancer, hepatic dysfunction, malignancies, AIDS, trauma, burns, sepsis, pulmonary disease, Parkinson's disease, diabetes, Alzheimer's, Schizophrenia, cystic fibrosis, heart attack and stroke, seizures, Sickle Cell Anemia, bipolarism, chronic fatigue syndrome, autism, and related immunologic illnesses and physiological conditions (e.g. Kidd, Alternative Medicine Review, 1997, 2(3): 156-176).

Direct supplementation of GSH is difficult as oral GSH is not well absorbed by the gastrointestinal tract (Witschi, et al. (1992), European Journal of Clinical Pharmacology, 43(6): 667-669). U.S. Pat. No. 7,446,096 describes a delivery system that includes glutathione covalently bound to PEG, which is covalently bound to a phospholipid, which is then intercalated into a liposome carrier. Further, a study of liposome-encapsulated GSH distribution when administered to the lung showed that the GSH was confined to the lung (Romet et al., Int. J Pharma., 63(3).227-235). Lipoceutical™ Glutathione is an oral form of liquid, liposome-enclosed glutathione that is currently available. Each teaspoon (5 mL) contains 422.7 mg of glutathione (per ingredient list).

There is no Recommended Dietary Allowance (RDA) for GSH, but supplements have no known harmful side effects (website at vitaminstuff.com/glutathione.html). In embodiments, an effective amount of liposome entrapped GSH is administered. The exact dose required for treatment or prevention may be determined by administration of a trial dose and observation of the clinical response. In general, an effective amount to be administered will be within a range of from about 0.1 mg/kg to about 50 mg/kg of body weight. In other embodiments, about 0.5 mg/kg to about 25 mg/kg daily is administered. In further embodiments, about 50-1, 000, 50-2,000, 50-3,000, 50-4,000, 50-5000 mg, and 50-10,000 mg is administered daily. Preferably, about 50-500 mg is administered daily.

a. Methods of Use of Liposome-Entrapped Glutathione

Cancer

In one aspect, liposome-entrapped GSH is administered to prevent, treat, or ameliorate the symptoms of cancer. Many cancers develop due to damage to cellular DNA, which results in uncontrolled and autonomous growth and multiplication of the damaged cells. One theory is that damage to cellular DNA is often caused by exposure to free radicals. As an antioxidant, GSH reacts with the free-radicals to prevent their contact with DNA and thus, prevent the cancer causing damage.

Preliminary results from a recent study indicate that glutathione changes the level of reactive oxygen species in isolated cells grown in a laboratory, which may reduce cancer development (Park, Oncology Reports, 2009, 385-391). A 1993 animal study showed GSH inhibited the development of oral carcinogenesis. Animals given oral supplementation of GSH after exposure to DMBA demonstrated significantly fewer and smaller tumors than the untreated control group (Yance, et al., *Herbal Medicine, Healing and Cancer*, Keats Publishing, 1999). A further study showed that women with ovarian cancer who were being treated with chemotherapy (cisplatin) and were also treated with intravenous glutathione had fewer side effects from the chemotherapy and could tolerate more cycles of treatment, but also had better overall survival rates (Yance et al.).

Administration of GSH along with conventional radiation and chemotherapy for the treatment of cancer has been shown to improve prognosis. Administration of GSH along with an oxaliplatin/5-fluoroacil/leucovorin regimen in colorectal cancer reduced neurotoxicity as compared to administration of the regimen alone (Milla et all., 2009, Anticancer Drugs, 20(5):396-402). In embodiments, liposome-entrapped GSH is co-administered (before, after, or concurrently) with chemotherapeutic agents to lessen, prevent, or relieve the toxic effects of the chemotherapeutic agent. GSH may be co-administered with chemotherapeutic agents including, but not limited to, the vinca alkaloids, such as vincristine and vinblastine, taxol and derivatives such as taxotere, anthracyclines, and platinum-based drugs such as cisplatin (U.S. Pat. No. 5,618,823, which is incorporated herein by reference).

AIDS

Acquired Immune Deficiency Syndrome (AIDS) refers to a number of infections and symptoms that are the result of damage to the immune system caused by exposure to the human immunodeficiency virus (HIV) retrovirus. As the condition advances, affected individuals are increasingly at risk for opportunistic infections and tumor growth. Additionally, HIV-infected patients have a higher incidence of oxidative stress, endothelial dysfunction, and cardiovascular disease than uninfected individuals (Kline, et al., Am. J. Physiol. Heart Circ. Physiol., 2008, 294(6):H2792-H2804). A study using an HIV-1 rat model showed that restoring glutathione levels, by administering GSH precursors, reversed the HIV1 protein-mediated effects on superoxide, NO and vasorelaxation (Kline et al.). Administration of GSH may also treat AIDS by boosting the immune system and preventing opportunistic infections. Treatment of blood cells isolated from HIV-infected subjects with a GSH precursor caused improved control of intracellular M. tuberculosis infection (Venketaraman, et al., 2006, AIDS Res. Ther., 3:5). GSH has also been shown to have an antiviral effect at the late stages of virus replication (Garaci, et al., 1997, J. Leukoc. Biol., 62(1),54-59). Low GSH levels in HIV patients predicted poor survival in otherwise indistinguishable HIV-infected subjects (Garaci et al.). In one embodiment, liposome-entrapped GSH is administered to treat or prevent HIV infection or AIDS. In another embodiment, liposome-entrapped GSH is administered to treat or prevent opportunistic infections and diseases associated with HIV and AIDS.

Burns

A burn is an injury to the skin, which may be caused by exposure to heat, electricity, chemicals, light, radiation, friction or cold. Burns may be complicated by shock, infection, and respiratory distress. Burns are traditionally divided into classifications of first-, second-, third-, fourth-, fifth-, or sixth-degree. First-degree burns are usually limited to superficial injury to the epidermis. Second-degree burns involve injury to the superficial (papillary) dermis and may also involve the deep (reticular) dermis layer. Second-degree burns may also involve nerve damage. Third-degree burns involve epidermis loss and damage to the subcutaneous tissue. Fourth-degree burns involve destruction of the dermis and damage to the muscle. Fifth-degree burns involve destruction of the epidermis, dermis, and subcutaneous tissue. Sixth-degree burns involve destruction of the epidermis, dermis, subcutaneous tissue, and muscle. These burns can also involve charring of the bone. A newer classification divides burns into thickness (superficial and partial) and depth (superficial and deep). In addition to the benefit to the immunological system, the use of GSH has been shown to be effective for saving the zone of stasis, one of the goals of burn treatment (Zor, et al., 2005, Burns, 31(8):972-976. In one embodiment, liposome-entrapped GSH is administered to treat burns.

3. Alpha-Lipoic Acid

Alpha-Lipoic Acid (ALA) is an antioxidant found in the body. Unlike other antioxidants which are only water-soluble or fat-soluble, ALA is both fat- and water-soluble. Evidence also suggests that ALA has the capacity to regenerate other antioxidants (Jones et al., Free Radio Biol Med., 2002, 33(1):83-93.).

The C6 carbon atom of ALA is chiral and the molecule exists as R and S enantiomers. The R-(+)-lipoic acid (R-LA) is an essential cofactor for several mitochondria i enzyme complexes that catalyze critical reactions related to energy production and the catabolism (breakdown) of alpha-keto acids and amino acids (Bustarnante, et al., Free Radic Biol Med. 1998, 24(6):1023-1039). R/S racemic mixtures (R/S-LA) and R-LA are widely available as over-the-counter nutritional supplements in the United States in the form of capsules, tablets and aqueous liquids, Additionally, a liposomal ALA skin cream is available (Reviva Labs), Although ALA is present in many foods, consumption of ALA from foods has not yet been found to result in detectable increases of free ALA in human plasma or cells (Hermann et al., Eur J Pharm Sci. 1996, 4:167-174). In contrast, high oral doses of free ALA (50 mg or more) result in significant but transient increases in free ALA in plasma and cells (Ipi.oregonstate.edu/infocenter/othernuts/la/). Pharmacokinetic studies in humans have found that about 30-40% of an oral dose of R-LA is absorbed (Hermann et al.). Alpha-lipoic acid can be purchased in doses of 30-100 mg tablets.

There is no RDA for ALA, but supplements have no known harmful side effects when taken at labeled doses. High doses may cause upset stomach, nausea, diarrhea, and flatulence (see nutritional-supplements-health-guide.com/alpha-lipoic-acid-side-effects.html). In embodiments, an effective amount of liposome entrapped ALA is administered. In one embodiment, the liposome composition includes the R-enantiomer of ALA. In another embodiment, the liposome composition includes a racemic mixture of ALA. The exact dose required for treatment or prevention may be determined by administration of a trial dose and observation of the clinical response. In embodiments, about 10-10,000 mg is administered daily. In further embodiments, about 10-50, 10-100, 10-500, 10-1000, 20-100, 20-500, 20-100, 50-100, 50-200, 50-300, 50-400, 50-600, 50-800, 50-900, 50-1,000, 50-2,000, 50-3,000, 50-4,000, 50-5,000, and 50-10,000 mg is administered daily. Preferably, about 50-500 mg is administered daily. For general antioxidant benefits, in one embodiment, 20-50 mg per day is administered. It will be appreciated that the doses may be administered as a divided dose two or more times per day.

In one non-limiting embodiment, the liposomes contain about 2.5-10 wt % of ALA (Na ALA or Na R-ALA). In other embodiments, the liposomes contain at least about 2.5-5 wt % of ALA. It may be preferable to have a wt % of less than about 7.5% in order to prevent or reduce phase separation. As described in Example 9, liposomes were found be highly stable with 90% of the entrapped ALA being retained within the liposomes after storage for 50 days at room temperature or at high temperature (40° C.). In non-limiting embodiments, the ALA entrapped liposomes are stable for at least about 1-3 months. In a preferred embodiment, the ALA entrapped liposomes are stable for at least about three months.

a. Methods of Use of Liposome-Entrapped ALA

In embodiments, ALA may be use to treat or prevent oxidative stress or damage (Toklu et al., J. Spinal. Cord Med., 2010, 33(4):401-409), diabetes, liver disease, inflammation (Odabasoglu, et al., Br, J. Nutr., 2010, Nov. 15: 1-12), neurodegenerative diseases such as Alzheimer's (Zara, et al., Exp. Gerontol., 2010, Nov. 8), cardiovascular disease, peripheral nerve injuries (Ranieri, at al., J. Brachial. Plex. Peripher. Nerve Inj., 2010, 5:15), schizophrenia (Seybolt, Med. Hypotheses, 2010, 75(6):572-575), obesity (Carbonelli, at al., Curr. Pharm., Des., 2010, 16(7):840-846), cancer (Schwartz, Oncol., Rep., 2010, 23(5):1407-1416), and hypertension (Kizhakekuttu, at al., Cardiovasc., Ther, 2010, 28(4):e20-e32).

Diabetes

Studies have shown that high doses of ALA can improve glucose utilization in individuals with Type 2 diabetes. A clinical trial in 13 patients with Type 2 diabetes found that a single intravenous infusion of 1000 mg of racemic ALA improved insulin-stimulated glucose disposal (insulin sensitivity) by 50% as compared to a placebo infusion (Jacob, at al., Arzneimittelforschung. 1995, 45(8):872-874). In a further placebo-controlled study of 72 patients with Type 2 diabetes, oral administration of racemic ALA at doses of 600 mg/day, 1200 mg/day or 1800 mg/day improved insulin sensitivity by 25% after 4 weeks of treatment (Jacob et al., Biofactors, 1999, 10(2-3):169-174). The study showed no significant differences among the three doses of ALA, suggesting that 600 mg/day may be the maximum effective dose (Ziegler et al., Treat Endocrinol., 2004, 3(3):173-189). It has further been shows that ALA can lower blood sugar levels in diabetic patients (Melhem et al., J Am Soc Nephrol., 2002, 13:108-116).

The ability of ALA to remove free radicals helps reduce pain, burning, itching, tingling, and numbness in people who have nerve damage caused by diabetes (peripheral neuropathy) (Androne et al., In Vivo, 2000, 14(2):327-330). ALA has been used to treat peripheral neuropathy for years in Europe.

In another embodiment, liposomal ALA is used to treat vascular disease associated with or complicated by diabetes. The inner lining of blood vessels, known as the endothelium, plays an important role in preventing vascular disease. Endothelial function is often impaired in diabetic patients, who are at high risk for vascular disease (Schalkwijk et al., Clin Sci (Lond)., 2005, 109(2):143-159). Intra-arterial infusion of racemic LA has been shown to improve endothelium-dependent vasodilation in diabetic patients, but not in the healthy controls (Heitzer et al., Free Radio Biol Med., 2001, 31(1):53-61).

ALA is also used to treat the diabetes-related condition autonomic neuropathy, which affects the nerves supplying the heart. One study found that 73 people with autonomic neuropathy improved when taking 800 mg of alpha-lipoic acid orally compared to placebo (umm.edu/altmed/articles/alpha-lipoic-000285.htm).

In an embodiment, at least about 600-800 mg per day of liposome entrapped ALA is administered to a patient suffering from diabetes, diabetic neuropathy, and/or vascular complications from diabetes.

Liver Disease

ALA has been used in combination with silymarin and selenium in the treatment of hepatitis C (Berkson, Med Klin, 1999, 94(Suppl. 3):84-89). In this study, treatment of three patients with cirrhosis, portal hypertension and esophageal varices secondary to chronic hepatitis C infection with the antioxidants resulted in improved laboratory values. In one embodiment, liposome-entrapped ALA is administered to treat liver disease and/or hepatitis.

Stroke

Because alpha-lipoic acid can pass easily into the brain, it has protective effects on brain and nerve tissue. ALA is being investigating it as a potential treatment for stroke and other brain disorders involving free radical damage. Animals treated with alpha-lipoic acid, for example, suffered less brain damage and had a four times greater survival rate after a stroke than animals who did not receive this supplement (Panigrahi et al., Brain Res., 1996, 717(1-2):184-188). In one embodiment, liposome-entrapped ALA is administered to treat stroke.

HIV/AIDS

Supplementation with ALA also positively impacts patients with HIV and AIDS by restoring blood total GSH levels and improving functional reactivity of lymphocytes to T-cell mitogens (Jariwalla, et al., 2008, J. Altern. Complement Med., 14(2):139-146). In one embodiment, liposome-entrapped ALA is administered to treat HIV and AIDS.

B. Pharmaceutical Agents

Pharmaceutical agents suitable for entrapment in liposomes using the cold process method include natural and synthetic compounds having the following therapeutic activities: anti-arthritic, anti-arrhythmic, anti-bacterial, anti-cholinergic, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemic alleviating, hyperglycemic alleviating, immunosuppressive, immunoenhancing, muscle relaxing, neurotransmitting, parasympathomimetic, sympathominetric plasma extending, plasma expanding, psychotropic, thrombolytic and vasodilating. In one embodiment, the pharmaceutical agent is a cytotoxic drug or agent, an anthracycline antibiotic selected from doxorubicin, daunorubicin, epirubicin, and idarubicin; a platinum compound including, but not limited to, cisplatin, carboplatin, ormaplatin, oxaliplatin, zeniplatin, enloplatin, iobaplatin, spiroplatin, ((-)-(R)-2-aminomethylpyrrolidine (1,1-cyclobutane dicarboxylato)platinum)(DWA2114R), (SP-4-3 (R)-1,1-cyclobutane-dicarboxylato(2-)-(2-methyl-1,4-butanediamine-N,N')platinum) (CI-973), nedaplatin (254-S) and (bis-acetato-ammine-dichloro-cyclohexylamine-platinum(IV)); a topoisomerase 1 inhibitor selected from, but not limited to, topotecan, irinotecan, (7-(4-methylpiperazinomethylene)-10,11-ethylenedioxy-20(S)-camptothecin), 7-(2-(N-isopropylarnino)ethyl)-(20S)-camptothecin, 9-aminocamptothecin, 9-nitrocamptothecin; a vinca alkaloid selected from, but not limited to, vincristine, vinblastine, vinleurosine, vinrodisine, vinorelbine, vindesine; an angiogenesis inhibitor including, but not limited to, angiostatin, endostatin, and TNF-alpha; and DNA and RNA based nucleic acids.

V. Unit Dose

In one embodiment, the liposome-entrapped nutritional supplement or composition is provided as a unit dose in a suitable container. Preferably, the container is a pouch or packet container of suitable size to contain the unit dose. The container may be formed of paper (coated or uncoated), foil, polymer, metal, plastic, puncture-resistant nylon film, or any combination thereof. In embodiments, the container is formed of foil-laminate, heat sealed laminate, or strip packaging. The container may be formed of one or more layers of a suitable material. The container may also be formed of layers of different suitable materials. In one embodiment, the container is formed of one or more layered sheets of a suitable material(s). For example, the inner layer that contacts the supplement or composition may be formed of an inert material that does not react with the ingredients of the supplement or composition. The inner layer may also be formed of a material that is impermeable to moisture, air, and or light. The outer layer may be formed of a material that is suitable for labeling. In one embodiment, the container is formed of a multilayer laminate. In this embodiment, the inner layer may be formed of a material that provides a vapor barrier, prevents evaporation of the composition, and/or prevents degradation by UV and other light sources. In one embodiment, the inner layer is a metal such as aluminum. In another embodiment, the container is formed of one or more thermoplastic polymer sheets. Suitable thermoplastic polymers include, but are not limited to, polyethylene, polypropylene, polyvinyl chloride, polystyrene, polytetrafluoroethylene, acrylonitrile butadiene styrene, and polyamide or combinations thereof.

Where the container is formed of a single piece of material(s), the piece is preferably folded and sealed along at least two edges leaving one side open for filling with the unit dose. Where the container is formed of two or more pieces of material(s), three of the sides are sealed by any suitable means leaving one side open for filling with the unit dose. In this manner, the container has an open, inner portion for filling with the unit dose.

Figure 2A:
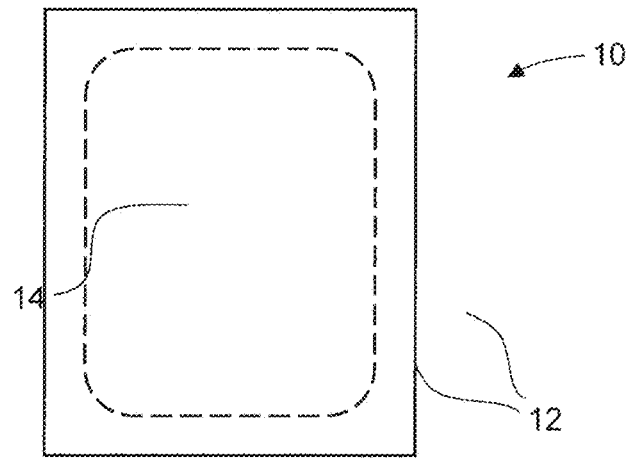
FIGS. 2A-2B shows side and top views of an exemplary container.
Figure 2B:
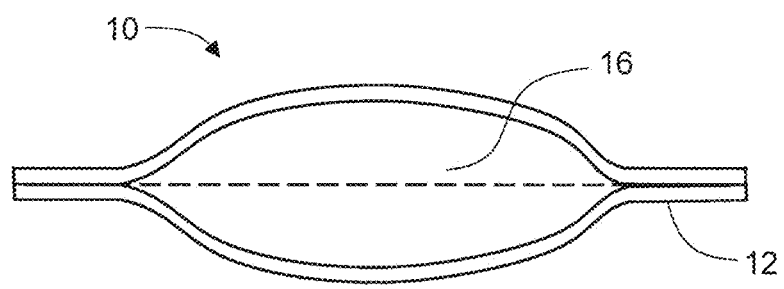

An exemplary container is shown in FIGS. 2A-2B. As seen in FIG. 2A, the container 10 may be formed of two opposing sheets that are sealed at the edges 12 leaving the interior 14 unsealed. As seen in FIG. 2B, one edge may initially be left unsealed to form a fillable area 16 for holding a product such as the liposome composition. After filling the container, this edge may further be sealed.

A suitable dose of the liposome composition is dispensed into the inner portion of the container. Once the liposome composition dose is dispensed into the container, the opening on the remaining side is sealed. The container may be sealed under an inert gas such as $N_2$. Sealing the container under an inert gas may improve the stability of certain entrapped agents such as vitamin C. The container sides may be sealed by any suitable means including thermal sealing or use of a suitable adhesive. The container sides may be thermally sealed by applying an amount of heat sufficient to at least partially melt at least part of the material(s) forming the container. In this manner, the sides of the container are laminated together. In other embodiments, the container may be thermally sealed with sonic welding. In another embodiment, the container may be sealed with a suitable adhesive. Suitable adhesives include, but are not limited to, acrylic polymers and copolymers, natural latex rubber, and vinyl acetate. The container may further be sealed by a zipper closure. The container may further include a peel section to allow for ease in opening the container after it is sealed.

VI. Examples

The following examples are illustrative in nature and are in no way intended to be limiting.

Example 1

Preparation of Sodium Ascorbate Entrapped Liposomes 97 g Phospholipon 50IP (a non-GMO vesicle-forming phosphatidylcholine lipid available from Lipoid) was solubilized in 56.3 g 200 proof alcohol at room temperature. Care was taken to ensure that all lipids were completely solubilized and no undissolved lipid remained. 109,5 g sodium ascorbate and 26.4 mg EDTA was separately solubilized in 251 g reverse osmosis-treated water at room temperature with normal agitation. The pH of the Na ascorbate-EDTA solution was adjusted to 6.3 The sodium ascorbate-EDTA solution was filtered with a 0.2 µm filter to remove dust particles and other contaminants. Streams of the lipid solution were slowly injected into the vitamin solution with continuous vortexing with a mixer. After all the lipid solution was added, lipid hydration was allowed to continue about 15 minutes with frequent mixing. At this point, the liposomes had formed in a smooth, translucent fluid.

2.2 g xanthan gum (available from Sigma-Aldrich®) and 1.38 g Tween™ 80 (available from SigmaAldrich®) were added to thicken the solution into a gel. The resulting liposome solution was transparent with a honey-like color.

Example 2

Comparison of Empirical Liposomes and LivOn Liposomes

Several batches of Lypo-Spheric™ Vitamin C liposomes were obtained from LivOn Laboratories. According to the product ingredient table, each 5.7 mL packet of Lypo-Spheric™ Vitamin C liposomes contains 1,000 mg of sodium ascorbate and 1.0 g of essential phospholipids. The Lypo-Spheric™ Vitamin C liposomal product ranged in color from light orange to brownish. A second commercial product, Liposomal Vitamin C liposomes, were obtained from Empirical Laboratories. According to the product ingredients table, each 4 mL serving size of Empirical Liposomal Vitamin C liposomes contains 1000 mg sodium ascorbate and 400 mg of phosphatidylcholine.

The LivOn and Empirical liposome formulations were compared for sodium ascorbate amounts, particle size, amount of dry material and amount of lipid (estimated) with the results shown in Table 2. The Empirical liposomes appeared dilute in comparison to the LivOn liposomes. The Empirical liposomes separated into two layers when left on the bench for a relatively short period of time (<1 hour). Upon centrifugation of the separated Empirical liposomes, the lower layer accounted for about 70-80% of the total volume. Both layers of the Empirical liposomes were a brownish color and relatively transparent. The lower layer was more water-like and the top layer was more gel-like. The Empirical product became turbid and more viscous upon mixing by hand shaking.

The amount of sodium ascorbate in the liposomes was determined by HPLC. Sodium ascorbate encapsulation was determined by first separating free sodium ascorbate by centrifuge filtration. 200 µg of the product was weighed and diluted in 10 mL of 0.5M NaCl solution. The mixture was vortexed to completely disperse the liposomes in the buffer. This solution was further diluted 10× with 80/20% Ethanol/water to obtain a clear solution and assayed for total ascorbate concentration by HPLC. To determine the amount of free ascorbate, a small volume of about 0.5-1 mL of the solution was loaded into a centrifuge concentrator (Nanosep® 10K OMEGA pin OD010034 available from Pall Corp., or Millipore's Biomax UFV5BTK25 30K) and centrifuged for 1-2 hours. The filter has very fine pores which allows only aqueous solution containing free (non-encapsulated) sodium ascorbate to pass through while retaining the liposomes. The filtrant was then diluted 10× in 80/20% Ethanol/water. The sodium ascorbate concentration in the filtrant was measured by HPLC and compared against the total sodium ascorbate concentration to determine the encapsulation efficiency.

To evaluate the amount of dry material in the liposomes, an appreciable amount of the product was dried for 2-3 days in a freezer dryer. The weight change post vacuum drying was determined.

Particle size was determined by dynamic light scattering (NiCOMP 370) after dilution in saline. The solutions were vortexed to ensure complete dispersion of the liposomes. Three measurements were taken for the Empirical liposomes resulting in a mean particle size of 620-760 nm and standard deviation of 460-615 nm. Two separate batches of the LivOn liposomes were measured for particle size. Batch L0809 (newer) had a mean particle size of about 1200 nm and a broader distribution (SD 760 nm) as compared to batch L1208 (older). Batch L1208 had a mean particle size of about 800 nm and a standard deviation (SD) of 450 nm. In comparison, the particle size for liposomes prepared by the cold process described herein are typically in the range of 300-500 nm.

In separate experiments, 17 containers from 5 batches of LivOn liposomes were measured for particle size. The mean particle diameter ranged from less than 850 nm to over 1200 nm with an average mean particle size of 1030±100 nm. There was no statistical difference in particle size between the batches tested. The width of the particle size peak averaged about 740±60 nm with no statistical difference between the batches.

To measure pH, a small amount of product was diluted in MilliQ water. The mixture was vortexed to completely disperse the liposomes. The pH was measured using a standard laboratory pH meter.

The Empirical liposomes and the LivOn liposomes were observed under microscope. The Empirical liposomes had a number of very large oil droplets under microscopic viewing. Since oil droplets are essentially transparent to the laser beam of the particle sizing instrument, the measured particle size in Table 2 does not account for the effect of the oil droplets. The product ingredient list for the Empirical liposomes includes olive oil, vitamin E and flavor. Any one of these could account for the large oil droplets seen in the product. Further, the oil could be from the lipid raw material if low grade lipids were used in making the Empirical liposomes. The diluted Empirical liposome solution appeared less homogenous than the LivOn solution under microscope viewing.

TABLE 2

Comparison of Empirical Laboratory Liposomes and LivOn Liposomes

|  | Empirical Laboratories Lipo C (dose 4.58 g or 4 mL) | LivOn Laboratories Lypo-Spheric ™ Vitamin C (dose 6.5 g or 5.7 mL) |
|---|---|---|
| Sodium Ascorbate (w/w %) | 19.9 ± 0.6 | 17.1 ± 0.3 |
| Sodium Ascorbate (g/dose) | 09.1 ± 0.02 | 1.11 ± 0.04 |
| Ascorbic Acid (g/dose) | 0.81 ± 0.02 | 0.99 ± 0.04 |
| Sodium Ascorbate Encapsulation (%) | 7.4 ± 2.4 | 28 ± 1.4 |
| Particle Size (nm, mean ± SD) | 660 ± 510 | 1180 ± 760[1] |
| Amount of Dry Material (w/w %) | 40 ± 0.5 | 41 ± 0.5 |
| Lipid Content (est., w/w %) | 18.2 ± 0.2 | 19.5 ± 0.3 |
| pH | 7.0 | 5.5 |

[1] An older batch tested had a particle size of 800 nm ± 450 nm.

Example 3

Comparison of Cold Process Liposomes to LivOn Laboratories Liposomes

Cold process liposomes were prepared essentially as described in Example 1, Lypo-Spheric™ Vitamin C liposomes were obtained from LivOn Laboratories. Various properties of the liposome formulations were determined with the results shown in Table 3.

The weight percent of ascorbic acid in the liposome formulations was determined by HPLC. The alcohol content was determined by gas chromatography. Mean particle size was determined by dynamic light scattering. Sodium ascorbate encapsulation was determined by filtration and HPLC as described in Example 2.

TABLE 3

Comparison of Cold Process Liposomes and LivOn Liposomes

|  | Cold Process Liposomes | LivOn Laboratories Lypo-Spheric ™ Vitamin C |
|---|---|---|
| Vitamin C (ascorbic acid) % | 19.6% | 16.5% |
| Phospholipids (wt %) | 18.8% | 18.7% |
| Alcohol | 10-11% | 9-10% |

TABLE 3-continued

Comparison of Cold Process Liposomes and LivOn Liposomes

| | Cold Process Liposomes | LivOn Laboratories Lypo-Spheric ™ Vitamin C |
|---|---|---|
| Mean particle size (nm) | 300-450 | 800-1200 |
| Particle size distribution SD (nm) | 150-200 | 600-900 |
| Sodium ascorbate encapsulation (%) | 35 | 35 |
| pH | 6.3 | 6.0-6.5 |
| Vitamin C wt % change after 50° C. incubation (% of T = 0) | 95% (13 days) 94% (19 days) | 94% (13 days) 90% (19 days) |
| Appearance | yellow honey-like gel | Brownish yellow gel |

Example 4

Liposome Stability at Room Temperature and at High Temperature

The storage stability of the liposomes prepared by the cold process was investigated. Liposomes were prepared essentially as described in Example 1 except that Alcolec PC 50 lipids (a GMO phosphatidylcholine lipid available from American Lecithin Company) were used rather than non-GMO lipids. 2.0 mL plastic vials were filled with the liposomes and sealed with screw caps (each cap had a rubber O-ring for a complete seal) under $N_2$. The vials were stored at room temperature (25° C.) or high temperatures (50° C.).

The ascorbic acid content (wt %) was measured by HPLC for the liposomes stored at room temperature on day 4, 5, 7 (two measurements), 8, and 38. The ascorbic acid content (wt %) was measured by HPLC for the liposomes stored at high temperature on day 0, 5, 6 (two measurements), 11, 20, and 42. The results are shown in Table 4.

TABLE 4

Stability of liposomes stored at room temperature and at high temperature

| Storage at 25° C. | | Storage at 50° C. | | |
|---|---|---|---|---|
| day | ascorbic acid (wt %) | day | ascorbic acid (wt %) | % of T0 |
| 4 | 18.64 | 0 | 18.64 | 100.0 |
| 5 | 18.28 | 5 | 18.1 | 97.1 |
| 7 | 18.7 | 6 | 19.19 | 103.0 |
| 7 | 18.8 | 6 | 17.43 | 93.5 |
| 8 | 18.48 | 11 | 18.3 | 98.2 |
| 38 | 18.6 | 20 | 17.85 | 95.8 |
| | | 42 | 15.06 | 80.8 |

Example 5

Comparison of Liposome Stability for Storage at 50° C.

The stability of the cold process liposomes and the LivOn liposomes after storage at 50° C. was investigated. Cold Process Liposomes were prepared essentially as described in Example 1. LypoSpheric™ Vitamin C liposomes were obtained from LivOn Laboratories. The cold process liposomes were flushed with $N_2$ and then stored in 2.0 mL plastic vials. The LivOn liposomes were either stored in the original packaging or removed from the package, flushed with $N_2$ and then stored in 2.0 mL plastic vials. The ascorbic acid weight percent was determined by HPLC. The liposomes were then stored at 50° C. After 4, 13, or 19 days, the liposome compositions were removed and the ascorbic acid weight percentage was determined by HPLC with the results shown in Table 5. FIG. 4 is a graph comparing the stability of liposomes prepared by the cold process and Lypo-Spheric™ Vitamin C liposomes available from LivOn Laboratories over 19 days.

TABLE 5

50° C. Stability of Cold Process Liposomes and LivOn Liposomes

| | Cold Process Liposomes (in vials, $N_2$ flushed) | | LivOn Liposomes (in vials, $N_2$ flushed) | | LivOn Liposomes (in original packaging) | |
|---|---|---|---|---|---|---|
| day | ascorbic acid (wt %) | % of T0 | ascorbic acid (wt %) | % of T0 | ascorbic acid (wt %) | % of T0 |
| 0 | 19.6 | 100.0 | 16.7 | 100.0 | 16.7 | 100.0 |
| 4 | 18.1 | 92.3 | 16.5 | 98.8 | n/d | n/d |
| 13 | 19.19 | 97.9 | 15.7 | 94.0 | 16.6 | 99.3 |
| 19 | 17.43 | 88.9 | 15.0 | 89.8 | 16.6 | 99.5 |

In order to fully assess the stability of the liposome ascorbate prepared by the cold process, a large batch (14 kg) of liposome entrapped sodium ascorbate was manufactured. The amount of Na ascorbate was 22.1 wt % as determined by the weight of the components. The process of manufacturing was similar to the method described in Example 1 except that large containers (5 gallon pails) were used for lipid and vitamin C solubilization. An industrial homogenizer/blender was used for mixing the liposomes. The appearance of the final product was similar to that produced in Example 1. The end liposome ascorbate was filled 5.5 g per sachet by LivOn Labs in exactly the same way that commercial Lypo-Spheric™ Vitamin C liposomes were packed. The ascorbate stability was monitored at both 25 degree C. and 40 degree C. The HPLC assay results are shown in FIG. 6.

Example 6

Preparation of Reduced Glutathione Entrapped Liposomes 80 g Alcolec PC50 was solubilized in 48 g of 200 proof alcohol at room temperature. Care was taken to ensure that all lipids were completely solubilized and no undissolved lipid remained, 80 g glutathione reduced (GSH) was separately solubilized in 0.9% NaCl, 50 mM PO4, pH 3.9 at room temperature with normal agitation. 120 mg of EDTA was added to the GSH solution and completely dissolved. To produce the GSH encapsulated liposomes, a stream of the ethanolic lipid solution was slowly injected into the GSH solution with continuous mixing with a high speed blender. After all the lipid solution was added, lipid hydration was allowed to continue about 30-60 minutes with frequent mixing. At this point, the liposomes had formed in a smooth, yellow and turbid fluid. Particle size was measured with a dynamic light scattering instrument, ZetaPALS (Brookhaven). It was usually in the range of 200-600 nm.

To thicken the liposomes into a gel, 1.6 g Xanthan gum (available from Sigma-Aldrich®) was blended into the liposomes with mixing followed with 2.0 g Tween 80

(available from Sigma-Aldrich®). The finished product was a thick transparent gel with a honey-like color. The finished product had a theoretical GSH concentration of 20.0 wt %.

Example 7

HPLC Determination of Reduced Glutathione in Liposomes

The concentration of reduced glutathione in the liposome GSH formulation prepared in Example 6 was determined by a HPLC assay developed based on a published method (Raggi et al., 1997, Chromatographia, vol. 46, 17-22). The measured GSH concentration was 18.4±0.3 wt %, which is very close to the theoretical value of 20 wt %, indicating that nearly 92% of the starting GSH material remained stable during the formulation process.

Example 8

Preparation of Alpha Lipoic Acid Entrapped Liposomes 20 g of lipid Alcolec™ PC50 was solubilized in 12 g ethanol (200 proof alcohol) at room temperature. Care was taken to ensure that all lipids were completely solubilized and no undissolved lipid remained. 5.0, 7.5 or 10.0 g alpha lipoic acid sodium salt (Na ALA) or 5.0, 7.5 or 10 g of R-ALA sodium salt were separately solubilized in water containing 0.3% EDTA (pH 7.5) at room temperature with normal agitation. To produce the Na R-ALA encapsulated liposomes, the ethanolic lipid solution was slowly injected into the Na R-ALA solution with continuous mixing with a high speed blender. After all the lipid solution was added, lipid hydration was allowed to continue about 30-60 minutes with frequent mixing. At this point, the liposomes had formed in a smooth, yellow and turbid fluid.

To thicken the liposomes into a gel, 0.4 g xanthan gum was blended into the liposomes with mixing followed with 0.3 g Tween 80. The finished product was a thick turbid yellow gel. The finished product had a theoretical of Na ALA or R-ALA concentration of 5, 7.5 and 10.0 wt %.

Example 9

HPLC Determination of Lipoic Acid Liposome Potency and Stability

The stability of the Na-ALA and R-ALA liposomes prepared as described in Example 8 was investigated. For stability monitoring, glass vials were filled with the liposome formulations with no head space to minimize exposure to air and sealed with screw caps. Samples were stored at room temperature or at 40° C. It was found that there were several phase separations in the 10% Na-ALA and 10% Na R-ALA formulations in a few days with clear solution separating out at the lower part of the container. There was also obvious, but to a lesser degree, phase separation of the 7.5% Na ALA and Na-R-ALA, while the 5 wt % formulations stayed uniform for at least 8 weeks.

The 5 wt % Na-ALA and the 5 wt % R-ALA containing formulations were measured for their lipoic acid potency by a HPLC method developed in house based on a method "Analysis of Lipoic Acid Salts for Quality Assurance" published at GeroNova Research Inc web site (geronova-.com/sites/default/files/LA_HPLC_Mod_USP.pdf). The assay results are shown in Table 6 below. The results indicate that ALA encapsulated in liposomes produced using the cold process is very stable. It shows that the decrease in ALA or R-ALA potency after incubation for 50 days at either room temperature or 40° C. month is less than 10%.

TABLE 6

Stability of Na-ALA and R-ALA Liposomes Stored at Room Temperature and at 40° C.

| Formulation | ALA/R-ALA potency ratio | Stored at room temp. (wt %) | Stored at 40° C. (wt %) |
|---|---|---|---|
| 5 wt % Na-ALA liposomes | | 5.19% day 2 | 5.38% day 2 |
| | Day 50/day 2 | 4.87% day 50 94.0% | 5.27% day 50 98.0% |
| 5 wt % Na-R-ALA liposomes | | 5.15% day 2 | 5.60% day 2 |
| | Day 50/day 2 | 4.74% day 50 92.0% | 5.14% day 50 91.7% |

In a separate study, three Na-ALA liposome formulations containing 2.5, 5.0 or 7.5 wt % Na-ALA were prepared as described in Example 8. For stability monitoring, the liposomes were filled in glass vials with no head space and sealed with screw caps. Again, phase separation occurred in the 7.5 wt % ALA and the 7.5 wt % R-ALA formulations, The 5.0 wt % and the 2.5 wt % formulations remained uniform throughout the study. Samples were stored at room temperature or 40 degree C. and the ALA concentrations were determined by HPLC. The results are shown in Table 7. The results indicate that ALA encapsulated in liposomes produced using the cold process is very stable for at least three months. It further shows that the decrease in ALA potency from the end of first month to the end of the third month is less than 10% in all cases, even for formulations stored at 40 degree C. The HPLC measured values for the two 7.5% formulations are less accurate because the sampling was heterogeneous due to the phase separation of the formulations. There was no T=0 time point values due to the unavailability of the HPLC method at the time these formulations were prepared.

TABLE 7

Stability of Na-ALA Concentration in Liposomes After Storage

| Formulation # | Theoretical Na-ALA (wt %) | Na-ALA at room temp. (wt %) | Na-ALA at 40 C. by HPLC (wt %) |
|---|---|---|---|
| 1 | 7.5 | 6.52% 1 month | 8.26% 1 month |
| | | 5.63% 3 month | 7.78% 3 month |
| | Ratio 3 month/ 1 month | 86.4% | 94.1% |
| 2 | 5.0 | 5.25% 1 month | 5.66% 1 month |
| | | 4.83% 3 month | 5.17% 3 month |
| | Ratio 3 month/ 1 month | 91.3% | 92.1% |
| 3 | 2.5 | 2.62% 1 month | 2.63% 1 month |
| | | 2.42% 3 month | 2.53% 3 month |
| | Ratio 3 month/ 1 month | 92.4% | 96.3% |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope. All patents and publications cited above are hereby incorporated by reference.

It is claimed:

1. A method of making liposomes with an entrapped agent, comprising:
solubilizing at least about 10 w/w % of vesicle-forming lipids in about 1-12 w/w % of a solvent miscible with water at room temperature to form a lipid solution;
separately solubilizing about 2.5-25 w/w % of the agent in about 25-65 w/w % of an aqueous solvent and 0.005-0.01 w/w % of EDTA at room temperature to form an agent containing solution;
filtering the agent containing solution;
injecting a stream of the lipid solution into the agent containing solution while mixing; and
allowing the resulting lipid and agent containing solution to hydrate for at least one hour with frequent mixing;
wherein the w/w % is based on the weight of the liposome formulation with the entrapped agent, wherein the resulting liposomes retain at least about 65-100% of the entrapped agent after at least one month storage.

2. The method of claim 1, wherein the solvent miscible with water comprises an alcohol.

3. The method of claim 1, further comprising adding more lipid or a thickener to form a gel after the hydration step.

4. The method of claim 1, wherein the vesicle-forming lipids comprises at least about 45-50% phosphatidylcholine.

5. The method of claim 4, wherein the phosphatidylcholine is derived from egg or soy.

6. The method of claims 1-4, wherein the agent is ascorbic acid or a salt thereof.

7. The method of claim 1, wherein the agent is glutathione.

8. The method of claim 1, wherein the agent is alpha lipoic acid.

* * * * *

UNITED STATES PATENT AND TRADEMARK OFFICE
CERTIFICATE OF CORRECTION

PATENT NO. : 10,016,389 B2
APPLICATION NO. : 13/020730
DATED : July 10, 2018
INVENTOR(S) : Zhang Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 547 days.

Signed and Sealed this
Fourteenth Day of July, 2020

Andrei Iancu
*Director of the United States Patent and Trademark Office*